(12) United States Patent
Raylman et al.

(10) Patent No.: US 11,607,129 B2
(45) Date of Patent: Mar. 21, 2023

(54) COMBINED POSITRON EMISSION TOMOGRAPHY (PET)-ELECTRON PARAMAGNETIC RESONANCE (EPR) IMAGING DEVICE

(71) Applicant: West Virginia University, Morgantown, WV (US)

(72) Inventors: Raymond R. Raylman, Morgantown, WV (US); Alexander V. Stolin, Morgantown, WV (US); Valery V. Khramtsov, Morgantown, WV (US); Mark Tseytlin, Star City, WV (US)

(73) Assignee: WEST VIRGINIA UNIVERSITY, Morgantown, WV (US)

( * ) Notice: Subject to any disclaimer, the term of this patent is extended or adjusted under 35 U.S.C. 154(b) by 366 days.

(21) Appl. No.: 16/438,376

(22) Filed: Jun. 11, 2019

(65) Prior Publication Data
US 2019/0374105 A1    Dec. 12, 2019

Related U.S. Application Data

(60) Provisional application No. 62/683,350, filed on Jun. 11, 2018.

(51) Int. Cl.
*A61B 5/00* (2006.01)
*A61B 5/055* (2006.01)
(Continued)

(52) U.S. Cl.
CPC .......... *A61B 5/0035* (2013.01); *A61B 5/055* (2013.01); *A61B 6/037* (2013.01);
(Continued)

(58) Field of Classification Search
CPC ....... A61B 5/0035; A61B 5/055; A61B 6/037; A61B 5/0073; G01R 33/60;
(Continued)

(56) References Cited

U.S. PATENT DOCUMENTS

| 4,714,886 A | * | 12/1987 | Halpern | G01R 33/345 |
| | | | | 324/316 |
| 4,717,880 A | * | 1/1988 | Ono | G01R 33/345 |
| | | | | 324/318 |

(Continued)

OTHER PUBLICATIONS

Hyodo, Fuminori, et al. "Pulsed EPR imaging of nitroxides in mice." Journal of Magnetic Resonance 197.2 (2009): 181-185. (Year: 2009).*

(Continued)

*Primary Examiner* — Joel Lamprecht
*Assistant Examiner* — Nyrobi Celestine
(74) *Attorney, Agent, or Firm* — Thomas | Horstemeyer, LLP

(57) ABSTRACT

Described herein are positron emission tomography (PET)-electron paramagnetic resonance imaging (EPRI) systems and methods of use. In one example, a PET-EPRI system includes a PET-EPR insert, a PET scanner including one or more solid-state photodetectors, and a subject module that can house a subject for scanning. The PET-EPR insert includes an EPR resonator that can nest inside the PET scanner. The EPR resonator includes a resonator that can receive the subject module, a shield encircling the resonator and one or more rapid scan coils (RS-coils) positioned around the shield. The shield can prevent electrical coupling between the RS-coils and the resonator while being transparent to annihilation photons and magnetic field scans.

17 Claims, 18 Drawing Sheets

(51) Int. Cl.
G01R 33/60 (2006.01)
G01R 33/48 (2006.01)
A61B 6/03 (2006.01)
G01R 33/56 (2006.01)

(52) U.S. Cl.
CPC ......... *G01R 33/4808* (2013.01); *G01R 33/60* (2013.01); *A61B 5/0073* (2013.01); *G01R 33/5601* (2013.01)

(58) Field of Classification Search
CPC ............ G01R 33/4808; G01R 33/5601; G01R 33/481; G01N 24/10
See application file for complete search history.

(56) References Cited

U.S. PATENT DOCUMENTS

| | | | | |
|---|---|---|---|---|
| 2006/0251312 | A1* | 11/2006 | Krieg | A61B 6/037 600/407 |
| 2007/0102641 | A1* | 5/2007 | Schmand | G01R 33/381 250/363.04 |
| 2008/0054904 | A1* | 3/2008 | Neufeld | G01R 33/34046 324/318 |
| 2008/0284428 | A1* | 11/2008 | Fiedler | A61B 6/4417 324/307 |
| 2010/0001728 | A1* | 1/2010 | Blank | G01R 33/3808 324/316 |
| 2010/0021381 | A1* | 1/2010 | Woodard | A61K 49/0008 424/1.69 |
| 2011/0288401 | A1* | 11/2011 | Solf | A61B 6/4417 600/411 |
| 2012/0169341 | A1* | 7/2012 | McKinnon | G01R 33/481 324/318 |
| 2014/0187909 | A1* | 7/2014 | Saha | A61B 5/0035 600/411 |

OTHER PUBLICATIONS

Raylman, Raymond, Mark Tseytlin, and Alexander Stolin. "A combined PET-EPR system: initial testing." (2017): 396-396. (Year: 2017).*
Eaton, Sandra S., et al. "Rapid-scan EPR imaging." Journal of Magnetic Resonance 280 (2017): 140-148. (Year: 2017).*
H. Zaidi et al, "An outlook on future design of hybrid PET/MRI systems", Medical Physics, vol. 38, No. 10, pp. 5667-5689, Oct. 2011 (Year: 2011).*
Y. Shi et al., "Rapid scan electron paramagnetic resonance at 1.0 GHz of defect centers in γ-irradiated organic solids," Radiation Measurements, vol. 85, pp. 57-63, Dec. 2015 (Year: 2015).*
Hirata H, He G, Deng Y, Salikhov I, Petryakov S and Zweier J L 2008 A loop resonator for slice-selective in vivo EPR imaging in rats J. Magn. Reson. 190 124-34.
Bobko A A, Evans J, Denko N C and Khramtsov V V 2017b Concurrent longitudinal EPR 16 monitoring of tissue oxygenation, acidosis, and reducing capacity in mouse xenograft tumor models Cell Biochem. Biophys. 75 247-53.
Bauer C, Stalin A, Proffitt J, Martone P, Brefczynski-Lewis J, Lewis J, Hankiewicz J, 2 Raylman R and Majewski S 2013, Development of a ring PET insert for MRI IEEE Nuclear Science Symp. Conf. Record vol. 9 pp. 101-108.
Constantinides C, Mean R and Janssen B J 2011 Effects of isoflurane anesthesia on the cardiovascular function of the C57BL/6 mouse ILAR J. 52 e21-31 (PMCID:PMC3508701).
Elajaili H B, Biller J R, Tseytlin M, Dhimitruka I, Khramtsov V V, Eaton S Sand Eaton G R 4 2015 Electron spin relaxation times and rapid scan EPR imaging of pH-sensitive amino-substituted trityl radicals Magn. Reson. Chem. 53 280-4.
Ardenkjaer-Larsen J H, Laursen I, Leunbach I, Ehnholm G, Wistrand LG, Petersson J S 14 and Golman K 1998 EPR and DNP properties of certain novel single electron contrast agents intended for oximetric imaging J. Maan. Reson. 133 1-12.
Khramtsov V V, Bobko A A, Tseytlin M and Driesschaert B 2017 Exchange phenomena in the electron paramagnetic resonance spectra of the nitroxyl and trityl radicals: multifunctional spectroscopy and imaging of local chemical microenvironment Anal. Chem. 89 4758-71.
Komarov DA and Hirata H 2017 Fast backprojection-based reconstruction of spectral-12 spatial EPR images from projections with the constant sweep of a magnetic field J. Magn. Reson. 281 44-50.
Tseytlin M 2017 Full cycle rapid scan EPR deconvolution algorithm J. Magn. Reson. 281 272-8.
Epel B, Sundramoorthy S V, Krzykawska-Serda M, Maggio M C, Tseytlin M, Eaton G R, Eaton S S, Rosen G M, Kao J PY and Halpern H J 2017b Imaging thiol redox status in murine tumors in vivo with rapid-scan electron paramagnetic resonance J. Magn. Reson. 276 31-6.
Biller JR, Tseitlin M, Mitchell D G, Yu Z, Buchanan LA, Elajaili H, Rosen GM, Kao JP, 3 Eaton S S and Eaton G R 2015 Improved sensitivity for imaging spin trapped hydroxyl radical at 250 MHz ChemPhysChem 16 528-31.
Bobko A A, Eubank TD, Driesschaert B, Dhimitruka I, Evans J, Mohammad R, Tchekneva 15 EE, Dikov MM and Khramtsov V V 2017a Interstitial inorganic phosphate as a tumor microenvironment marker for tumor proQression Sci. Rep. 7 41233.
Smith MF, Raylman RR, Majewski Sand Weisenberger AG 2004 Positron emission 1 mammography with tomographic acquisition using dual planar detectors: initial evaluations Phys Med. Biol. 49 2437-52.
Pandian RP, Parinandi N L, Ilangovan G, Zweier J Land Kuppusamy P 2003 Novel particulate spin probe for targeted determination of oxygen in cells and tissues Free Radie Biol Med 35 1138-48.
Driesschaert B, Bobko A A, Eubank T D, Samouilov A, Khramtsov V V and Zweier J L 2016 Poly-arginine conjugated triarylmethyl radical as intracellular spin label Bioorg. Med. Chem. Lett. 26 17 42-4.
Stolin AV, Martone PF, Jaliparthi G and Raylman RR 2017 Preclinical positron emission 13 tomography scanner based on a monolithic annulus of scintillator: initial design study J. Med Imaging 4 011007.
Dhimitruka I, Grigorieva 0, Zweier J Land Khramtsov V V 2010 Synthesis, structure, and EPR characterization of deuterated derivatives of Finland trityl radical Bioorg Med. Chem. Lett. 20 3946-9.
Bowman M K, Mailer C and Halpern H J 2005 The solution conformation of triarylmethyl radicals J. Magn. Reson. 172 254-67.
Chano T, Avnet S, Kusuzaki K, Bonuccelli G, Sonveaux P, Rotili D, Mai A and Baldini N 17 2016 Tumour-specific metabolic adaptation to acidosis is coupled to epigenetic stability in osteosarcoma cells Am. J. Cancer Res. 6 859-75 (PMCID:PMC4859889).
Moser J, Lips R, Tseytlin M, Eaton GR, Eaton S Sand Schnegg A 2017 Using rapid-scan EPR to improve the detection limit of quantitative EPR by more than one order of magnitude J. Magn. Reson. 281 17-25.
Nadtochiy, Sergiy M et al. "Metabolomic profiling of the heart during acute ischemic preconditioning reveals a role for SIRT1 in rapid cardioprotective metabolic adaptation." Journal of molecular and cellular cardiology vol. 88 (2015): 64-72. doi: 10.1016/j.yjmcc. 2015.09.008.
Ewald, Andrew J et al. "Monitoring of vital signs for long-term survival of mice under anesthesia." Cold Spring Harbor protocols vol. 2011,2 pdb.prot5563. Feb. 1, 2011, doi:10 1101/pdb.prot5563.
Sekine, Kaori et al. "Oxygen consumption of human heart cells in monolayer culture." Biochemical and biophysical research communications vol. 452,3 (2014): 834-9. doi:10.1016/j.bbrc.2014.09.018.
Kishimoto, Shun et al. "Pulsed Electron Paramagnetic Resonance Imaging: Applications in the Studies of Tumor Physiology." Antioxidants & redox signaling vol. 28,15 (2018): 1378-1393 doi:10. 1089/ars.2017.7391.
Proffitt J, Hammond W, Majewski S, Popov V, Raylman R R, Weisenberger A G and Wojcik R 2005 A flexible high-rate USB2 data acquisition system for PET and SPECT imaging IEEE Nuclear Science Symp. Conf. Record pp. 2971-2975.

(56) References Cited

OTHER PUBLICATIONS

McKisson J E, Hammond B, Proffitt J, Weisenberger A G and Smit M 2007 A java distributed acquisition system for PET and SPECT imaging IEEE Nuclear Science Symp. Conf. Record vol. 1-11 p. 3591.

Wu H M, Huang S C, Choi Y, Hoh C Kand Hawkins R A 1995 A modeling method to improve quantitation of fluorodeoxyglucose uptake in heterogeneous tumor-tissue J. Nuc/. Med. 36 297-306 (PMID:7830134).

Epel B, Bowman MK, Mailer C and Halpern HJ 2014 Absolute oxygen R1e imaging in vivo with pulse electron paramagnetic resonance Maqn. Reson. Med. 72 362-8.

Eckert AW, Wickenhauser C, Salins P C, Kappler M, Bukur J and Seliger B 2016 Clinical relevance of the tumor microenvironment and immune escape of oral squamous cell carcinoma J. Transl. Med. 14 85.

Yamamoto S, Watabe T, Ikeda H, Kanai Y, Ichikawa K, Nakao M, Kato K and Hatazawa J 2016 Development of a PET/OMRI combined system for simultaneous imaging of positron and free radical probes for small animals Med. Phys. 43 5676-84.

Marchand V, Leveque P, Driesschaert B, Marchand-Brynaert J and Gallez B 2017 In vivo EPR extracellular pH-metry in tumors using a triphosphonated trityl radical Magn. Reson. Med. 77 2438-43.

Toyohara J, Elsinga PH, Ishiwata K, Sijbesma J W, Dierckx RA and van Waarde A 2012 Evaluation of 4'-[methyl-11 C] thiothymidine in a rodent tumor and inflammation model J. Nuc/. Med. 53 488-94.

Gorodetsky A A, Kirilyuk I A, Khramtsov V V and Komarov D A 2016 Functional electron paramagnetic resonance imaging of ischemic rat heart: monitoring of tissue oxygenation and pH Magn. Reson. Med. 76 350-8.

Epel B, Krzykawska-Serda M, Tormyshev V, Maggio M C, Barth E D, Pelizzari C A and Halpern H J 2017a Spin Lattice Relaxation EPR pO(2) Images may direct the location of radiation tumor boosts to enhance tumor cure Cell Biochem. Biophys. 75 295-8.

Proffitt J, Hammond W, Majewski S, Popov V, Raylman R R and Weisenberger A G 2006 Implementation of a high-rate USB data acquisition system for PET and SPECT imaging IEEE Nuclear Science Symp. Conf. Record vol. 1-6 pp. 3063-3067.

Khramtsov V V 2017 In vivo molecular EPR-based spectroscopy and imaging of tumor microenvironment and redox using functional paramagnetic probes Antioxid Redox Signal 28 1365-77.

Khramtsov V V and Gillies R J 2014 Janus-faced tumor microenvironment and redox Antioxid Redox Siqnal 21 723-9.

Wells J M, Mankoff D A, Eary J F, Spence A M, Muzi M, O'Sullivan F, Vernon C B, Link J M and Krohn K A 2002 Kinetic analysis of 2-[11C] thymidine PET imaging studies of malignant brain tumors: preliminary patient results Mol. maging 1 145-50.

Halpern H J, Yu C, Peric M, Barth E D, Karczmar G S, River J N, Grdina D J and Teicher B A 1996 Measurement of differences in pO(2) in response to perfluorocarbon carbogen in FSa and NFSa murine fibrosarcomas with low-frequency electron paramagnetic resonance oximetry Radiat. Res. 145 610-8.

Mitchell, Deborah G et al. "X-band rapid-scan EPR of samples with long electron spin relaxation times: a comparison of continuous wave, pulse and rapid-scan EPR." Molecular Physics, 2013vol. 111, Nos. 18-19, 2664-2673, http://dx.doi.org/10.1080/00268976.2013.792959.

Tseytlin, et al., (2018) A combined positron emission tomography (PET)-electron paramagnetic resonance imaging (EPRI) system: initial evaluation of a prototype scanner, Phys. Med. Biol. 63: 105010, 7 pages.

* cited by examiner

COMBINED POSITRON EMISSION TOMOGRAPHY (PET)-ELECTRON PARAMAGNETIC RESONANCE (EPR) IMAGING DEVICE

CROSS-REFERENCE TO RELATED APPLICATION

This application claims priority to U.S. Provisional application entitled "A COMBINED POSITRON EMISSION TOMOGRAPHY (PET)-ELECTRON PARAMAGNETIC RESONANCE (EPR) IMAGING DEVICE" having Ser. No. 62/683,350, filed on Jun. 11, 2018, which is entirely incorporated herein by reference.

STATEMENT REGARDING FEDERALLY SPONSORED RESEARCH

This invention was made with government support under grant number R21 EB022775 awarded by the National Institutes of Health. The Government has certain rights in the invention.

TECHNICAL FIELD

The present disclosure generally relates to combined position emission tomography (PET)-electron paramagnetic resonance (EPR) imaging devices and methods of use.

BACKGROUND

Understanding and manipulating tumor microenvironment (TME) is critical to the development of effective methods for cancer detection and treatment. TME, however, is a very complex biological system that is difficult to probe, especially in vivo. For example, the interaction between intracellular processes (glucose metabolism, for example) and the extracellular environment changes in response to these processes (pH, for example) are very difficult to simultaneously measure in vivo.

Imaging modalities for the measurement of intracellular processes and extracellular environmental changes currently exist. For example, both positron emission tomography (PET) and electron paramagnetic resonance imaging (EPR or EPRI) currently exist as standalone modalities for measuring intracellular processes and extracellular environmental changes, respectively. PET scanners are used in both the clinical and research applications. Currently, EPRI is only a research tool, utilized with small animal models of disease.

Current iterations of PET and EPRI as standalone modalities, while important tools, prevent temporal and/or spatial correlation of resultant images which precludes the use of both modalities to effectively monitor complex in vivo environments such as TME. Accordingly, there is a need to address the aforementioned deficiencies and inadequacies.

SUMMARY

Described herein are embodiments of PET-EPRI systems. In embodiments according to the present disclosure, PET-EPRI systems can comprise an EPR resonator comprising a resonator, one or more RS-coils, and a shield configured to prevent electrical coupling between the RS-coils and the resonator; and a PET scanner comprising one or more solid-state photodetectors.

In embodiments according to the present disclosure, the PET scanner can have a ring geometry with an inner diameter and the EPR resonator is configured to nest inside the inner diameter.

In embodiments according to the present disclosure, PET-EPRI systems as described herein can further comprise a subject module configured to house a subject for scanning, wherein the subject module resides within an inner diameter of the EPR resonator.

In embodiments according to the present disclosure, PET-EPRI systems as described herein can further comprise gradient coils surrounding an outer diameter of the PET scanner.

In embodiments according to the present disclosure, PET-EPRI systems as described herein can further comprise one or more magnets configured to provide a magnetic field to the EPR resonator. The one or more magnets can be permanent magnets or electromagnets, individually or in combination.

In embodiments according to the present disclosure, PET-EPRI systems as described herein can be configured to circulate cooling fluid through or within the EPR resonator, the PET scanner, or both.

In embodiments according to the present disclosure, PET-EPRI systems as described herein can further comprise a gantry configured to house electronic leads to and from the EPR module and PET scanner.

The subject module of PET-EPRI systems as described herein can be configured to modulate the temperature inside the module or of the subject.

The subject module of PET-EPRI systems as described herein can be configured to modulate anesthesia provided to a subject housed in the subject module.

The subject module of PET-EPRI systems as described herein can be configured to monitor physiological parameters of a subject housed in the subject module.

The one or more solid-state photodetectors of PET-EPRI systems as described herein can comprise one or more photomultipliers coupled to one or more radiation-sensitive scintillators.

In embodiments according to the present disclosure, PET-EPRI systems as described herein can further comprise one or more computing devices.

Also described herein are methods of combined PET-EPRI imaging or a subject, or methods of using a combined PET-EPRI system as described herein.

In embodiments according to the present disclosure, methods as described herein can comprise: providing the subject; positioning the subject in a subject module of a combined PET-EPRI imaging scanner; and imaging a region of interest (ROI) of the subject with the scanner. In embodiments of the present disclosure, the region of interest of a subject can be a tumor. In embodiments of the present disclosure, the region of interest of a subject can be a microenvironment of a tumor.

Methods as described herein can further comprise administering to the subject a PET probe, an EPRI probe, or both. Without intending to be limiting, in certain aspects, the PET probe can be fludeoxyglucose (also known as flurodeoxyglucose or $^{18}$F-fluorodeoxyglucose ($^{18}$F-FDG)). Without intending to be limiting, in certain aspects, the EPRI probe can be a trityl radical, such as phosphonated triarylmethyl radicals (pTAM).

In embodiments of the present disclosure, imaging the ROI of the subject can comprise collecting PET data from the ROI of the subject with the imaging scanner, EPRI data from ROI of the subject with the imaging scanner, or both.

In embodiments of the present disclosure, imaging can further comprise reconstructing an image of the PET scan from the PET data, an image of the EPRI scan from the EPRI data, or both.

In embodiments according to the present disclosure, methods as described herein can further comprise overlaying the image of the PET scan and image of the EPRI scan.

In embodiments according to the present disclosure, methods as described herein can further comprise monitoring physiological parameters of the subject before, during, or after the imaging, individually or in combination.

In embodiments according to the present disclosure, methods as described herein can further comprise modulating the temperature of the subject module. In embodiments according to the present disclosure, methods as described herein can further comprise modulating the temperature of the subject in the subject module subject module.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 7A shows results of EPRI alone, FIG. 7B shows results of PET alone, and FIG. 7C shows combined PET-EPRI scanning results.

FIG. 12A is an MRI image showing the presence and absence of Gd ($Gd^+$ or $Gd^0$), and the presence of high or low concentration of $^{18}F$ ($F^+$ or $F^-$). FIG. 12B is a PET image where the image intensity is related to FDG concentration. FIG. 12C is an EPR image of Lorentzian line width (EPRI-Lw) where the image intensity is related to oxygen concentration simulated using Gd. FIG. 12D is an EPR image of dFT concentration where the image intensity is related to dFT concentration.

FIG. 17A shows MOBY phantom with major brain sections labeled (cortex (Cort), thalamus (Thal), hypothalamus (Hypo), caudoputamen (Caud), ventricles (Vent) and amygdala (Amyg)) labeled, and FIG. 17B shows a PET image of the phantom.

DETAILED DESCRIPTION

Figure 1:
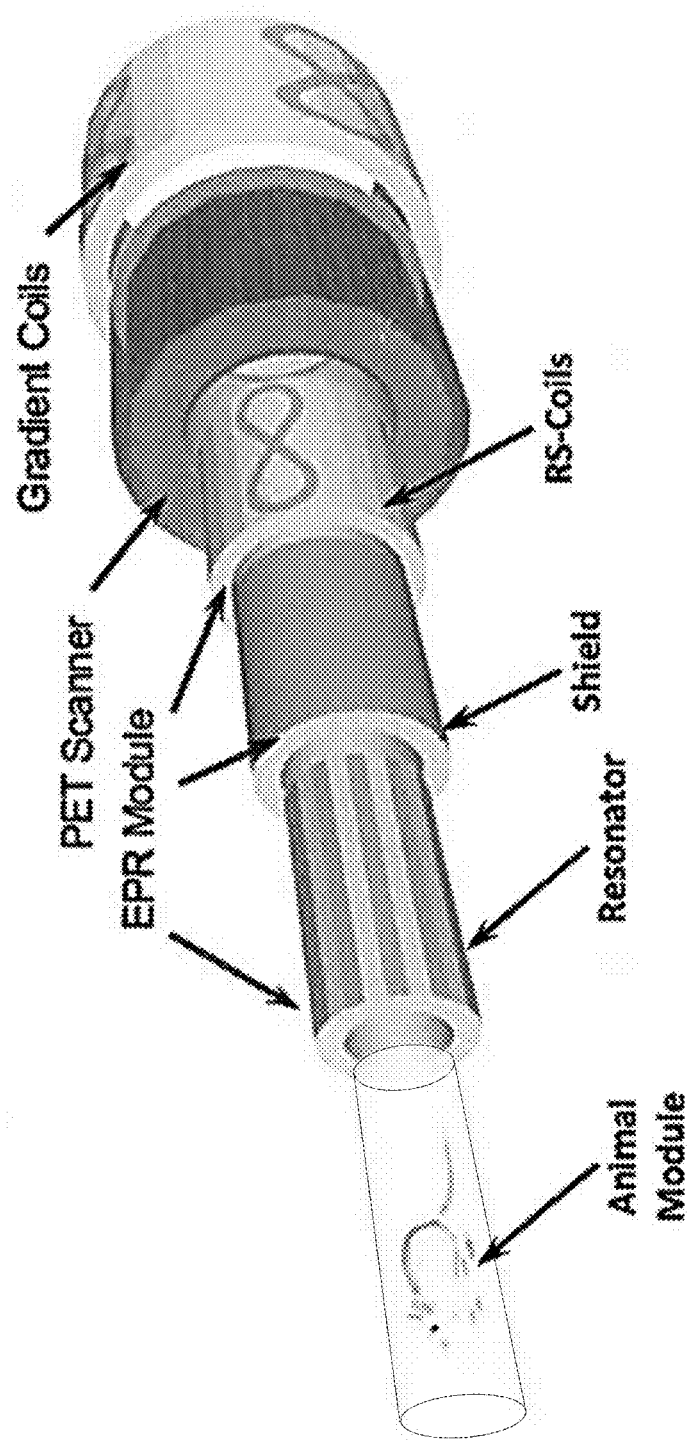
FIG. 1 is a schematic of an embodiment of a positron emission tomography-electron paramagnetic resonance imaging (PET-EPR or PET-EPRI) insert.

Described below are various embodiments of positron emission tomography-electron paramagnetic resonance imaging (PET-EPR or PET-EPRI) devices and methods of use. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

Discussion

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medical imaging, physics, mechanical engineering, biochemistry, cellular biology, cancer biology and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

It is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

Subjects

Subjects as defined herein can be any living being comprising living cells having intracellular and extracellular environments that can be monitored by imaging modalities in a research and/or clinical environment, such as positron emission tomography (PET) and electron paramagnetic resonance imaging (EPRI). Without intending to be limiting, subjects can be mammals (for example mice, rats, non-human primates, humans), amphibians (for example species of frogs), reptiles (for example snakes, lizards, and the like), and the like and can be beings which are the subject of non-invasive imaging techniques such as a Biochemical Agents As used herein, biochemical agents can refer to probes, labels, contrast agents, and the like, which the systems and scanners as described herein are configured to detect. Without intending to be limiting, these biochemical agents or probes or contrast agents can include radioisotopes or compositions comprising radioisotopes used by those skilled in the art for PET imaging, such as fludeoxyglucose (also known as flurodeoxyglucose), or compositions used by those skilled in the art for EPR imaging, such as trityl radicals or compositions containing trityl radicals (for example pTAM). Selection of probes for PET imaging and EPR spectroscopy/imaging is routine in the art, and one skilled in the art would be able to select one or more biochemical agents for use with the systems and methods described herein according to the desired application.

Description

The present disclosure is directed to positron emission tomography-electron paramagnetic resonance imaging (PET-EPR or PET-EPRI) devices and methods of use.

Combined imaging systems and embodiments thereof that combine positron emission tomography (PET) with electron paramagnetic resonance imaging (EPRI) are described herein, in addition to methods of use. Systems and methods as described herein can address challenges such as the simultaneous measuring of intracellular and extracellular components of complex pathological and non-pathological in vivo environments, for example the TME. Used in conjunction with PET radiotracers targeted to specific cellular functions (glucose metabolism: for example) and EPR probes targeting extracellular indices (pH and $pO_2$, for example), PET/EPRI scanners as described herein can be used to explore how cells such as cancer cells interact with and manipulate their environment, including invasion into adjacent normal tissue.

Performing these measurements using simultaneous imaging is important for further understanding of complex in vivo environments because environments such as the TME are not static. Therefore, any meaningful evaluation of the relationship between intra- and extracellular processes must be temporally correlated. Furthermore, simultaneous imaging greatly facilitates spatial correlation of the images from the two modalities, which is important to the correlation process. Systems and methods as describe herein permit the simultaneous PET and EPR imaging and address these issues. The advantages of systems and methods described herein include: temporal correlation of PET and EPRI;

spatial correlation of PET and EPRI; and both imaging modalities combined into one system, instead of two, which saves space and funds.

The combination of PET and EPRI is a unique concept in that it can be used to simultaneously image the biochemistry of living tissue using two different but complementary methods. Unlike other current scanners that combine functional and structural imaging modalities into a single system (PET with CT and PET with MRI), PET-EPRI combines two methods that measure functional parameters of tissue (tumors or heart muscle, for example). In one application, PET and EPRI could be used, with appropriate biochemical agents, to produce spatial distributions of intracellular and extracellular components of glucose metabolism in tumors. This information could be valuable for research and clinical applications.

The PET-EPRI systems described herein utilize a novel approach for combining imaging hardware and combine PET scanning hardware with EPR imaging hardware. In certain embodiments, the EPRI module is nested within a bore or inner diameter of the PET scanner, however in other embodiments, a nested design may not be employed and other hardware combinations can be realized.

The main elements of the system, such as the EPR resonator and PET scanner, can use a nesting paradigm, exemplified in FIG. 1, to produce a very compact system. As shown in FIG. 1, systems as described herein can comprise an EPR (or EPRI) module (or EPR resonator as described herein), a PET scanner, an animal module, and can additionally comprise gradient coils in certain embodiments. In certain aspects, gradient coils can produce a magnetic field strength as a function of position.

First, the main parts of the EPR resonator or EPRI system (resonator, shield and RS-coils) can be collapsed into a single physical structure called the EPR module or EPR resonator. Resonators as described herein can take on a variety of form factors as exemplified herein. A skilled artisan would recognize that the design of the shield can be dependent upon the form factor that best matches the desired application.

Figure 3A:
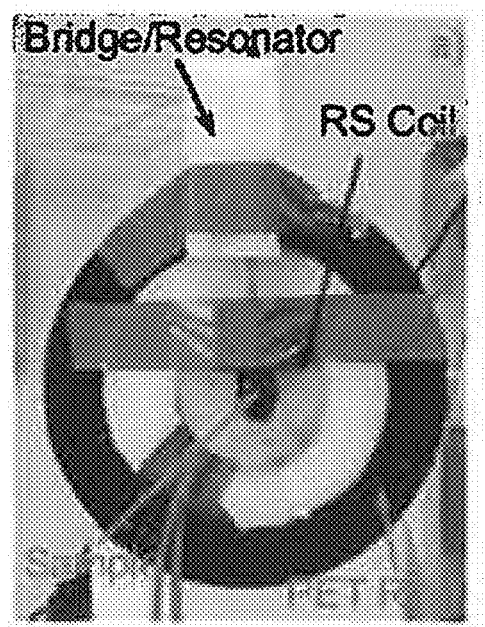
FIG. 3A is a photograph of an embodiment of a PET-EPR insert.
Figure 4:
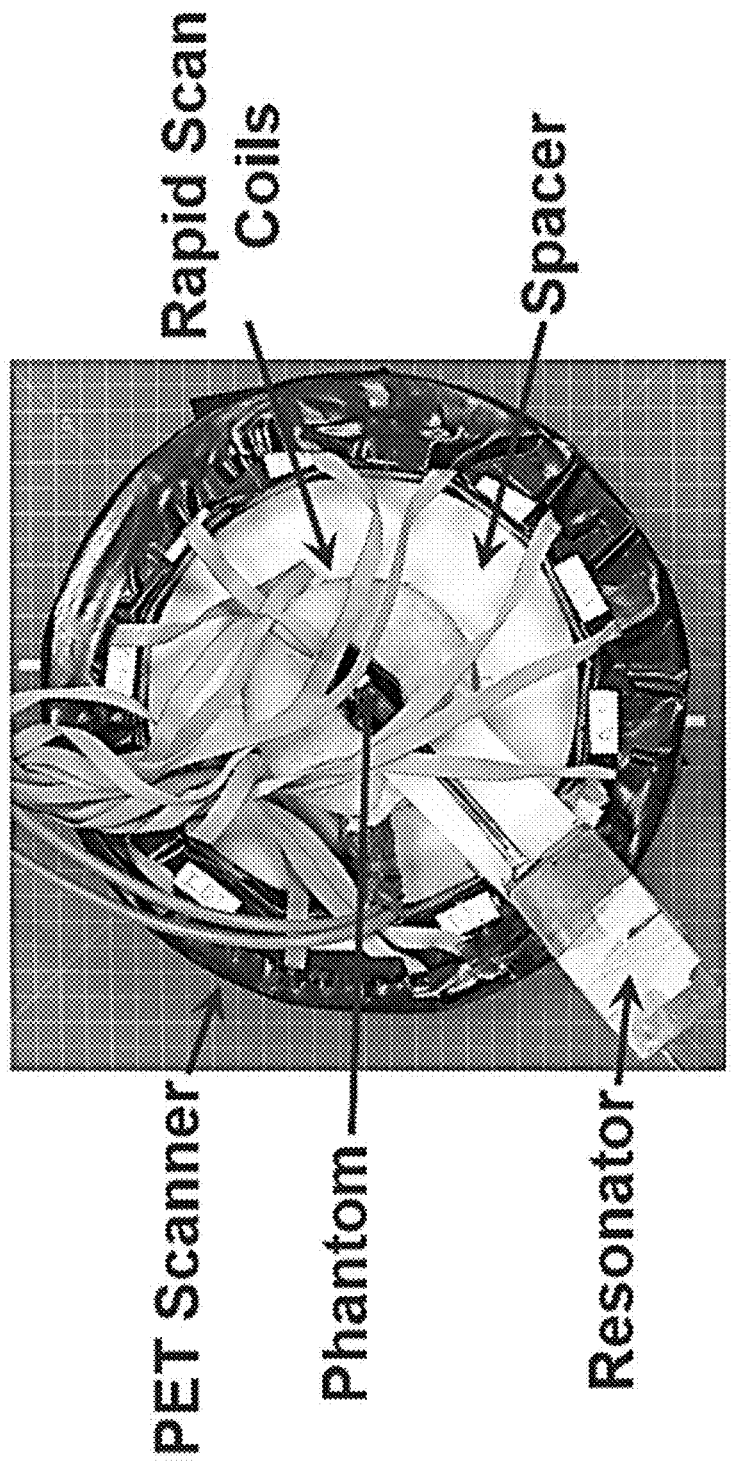
FIG. 4 is a photograph of an embodiment of a PET-EPRI insert

The rapid scan coils (RS-coils) can modulate the magnetic field to produce a large number of EPR signals that can be summed to increase accuracy. RS coils can provide the magnetic field scans and continuous wave (CW) radio frequency power is applied to excite the electron resonances, the resonator receives the signals from the excited electron resonances, and the shield prevents electrical coupling between the RS-coils and the resonator. The EPR module fits inside the PET scanner in a "nesting" paradigm, as shown in FIG. 1, FIG. 3A, and FIG. 4. In certain embodiments, the EPRI system can be an EPR resonator that comprises of a copper box (coupling and balun), coax cables and the resonator coil.

PET scanners described herein can take on a number of forms. In certain aspects, it can be based on a single annulus of radiation-sensitive scintillator. It certain aspects, it can be based on a series of individual detection units arranged in a ring geometry. The electrical components of the PET scanner can comprise of solid state photodetectors (which can comprise crystal scintillators, such as BGO, GSO, LYSO, coupled to silicon photomultipliers, for example) and read-out electronics. Examples of readout electronics which can be incorporated into systems as described herein are further described herein. These devices can be immersively cooled by circulating non-conductive, non-paramagnetic fluid (such as mineral oil, for example) through the PET scanner enclosure. The PET scanner can have an inner diameter or opening in which the EPR module can fit inside, or nest. This nesting design is shown throughout the figures, especially FIGS. 1, 3A, and 4. The EPR module-PET insert can be placed inside the gradient coils which can be used to apply spatially-varying magnetic fields in three-dimensions to permit the EPR images.

Finally, the module that houses the subject (which can be an animal, such as a mouse, rat, non-human primate, or other larger mammal) during scanning fits inside the PET-ERPI unit. This device has connections to permit circulation of anesthesia (necessary to immobilize the subject during scanning), physiological monitor, and temperature control.

The final element of the PET-EPRI system is the magnet necessary for inducing the net magnetization along the axis of the static magnetic field. Due to the physics of electron versus proton magnetic properties, the magnetic field necessary for EPRI is much lower than is required for MRI. Thus, it can be possible to utilize standard permanent or electro-magnets instead of superconducting magnets to supply magnetic fields for EPRI. A common way to supply EPRI magnetic fields is to use a dipole magnet (they are less expensive than a comparable solenoid magnet).

Figures 2A, 2B:
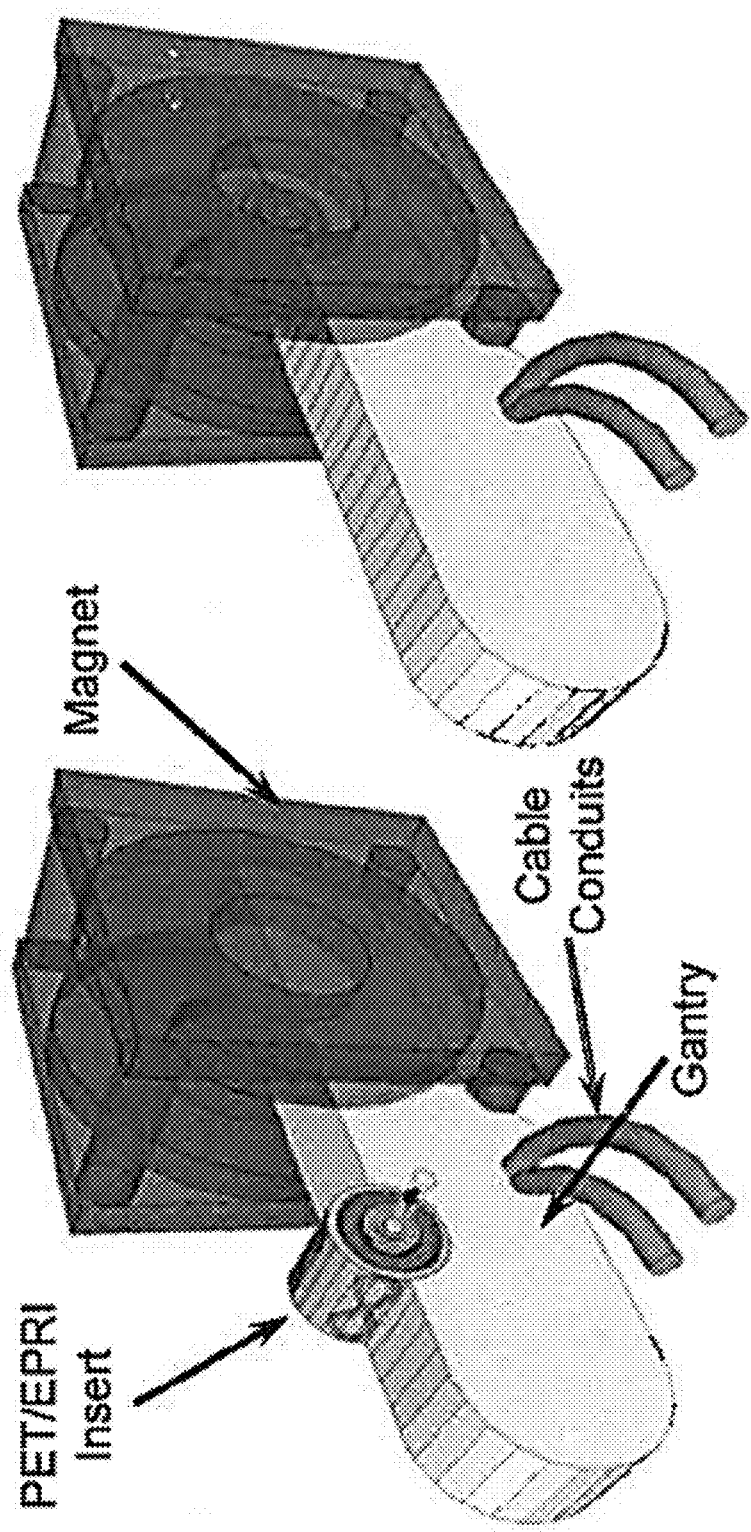
FIG. 2A is a schematic showing the complete PET-EPRI scanner in the loading position.
FIG. 2B is a schematic showing the complete PET-EPRI scanner in the scanning position.

To accommodate placement of the PET-EPRI unit into a dipole, it can be placed into a gantry (see FIGS. 2A and 2B). Specifically, the insert can be placed in a gantry receptacle. The electrical, cooling and animal module connections can be routed through the gantry to the insert. The insert can then be moved into the magnet for imaging with a device such as a motorized belt drive, the motor operated by a user or by a computing device. The gantry can be constructed from non-magnetic materials that produce no EPR signals.

Figure 14:
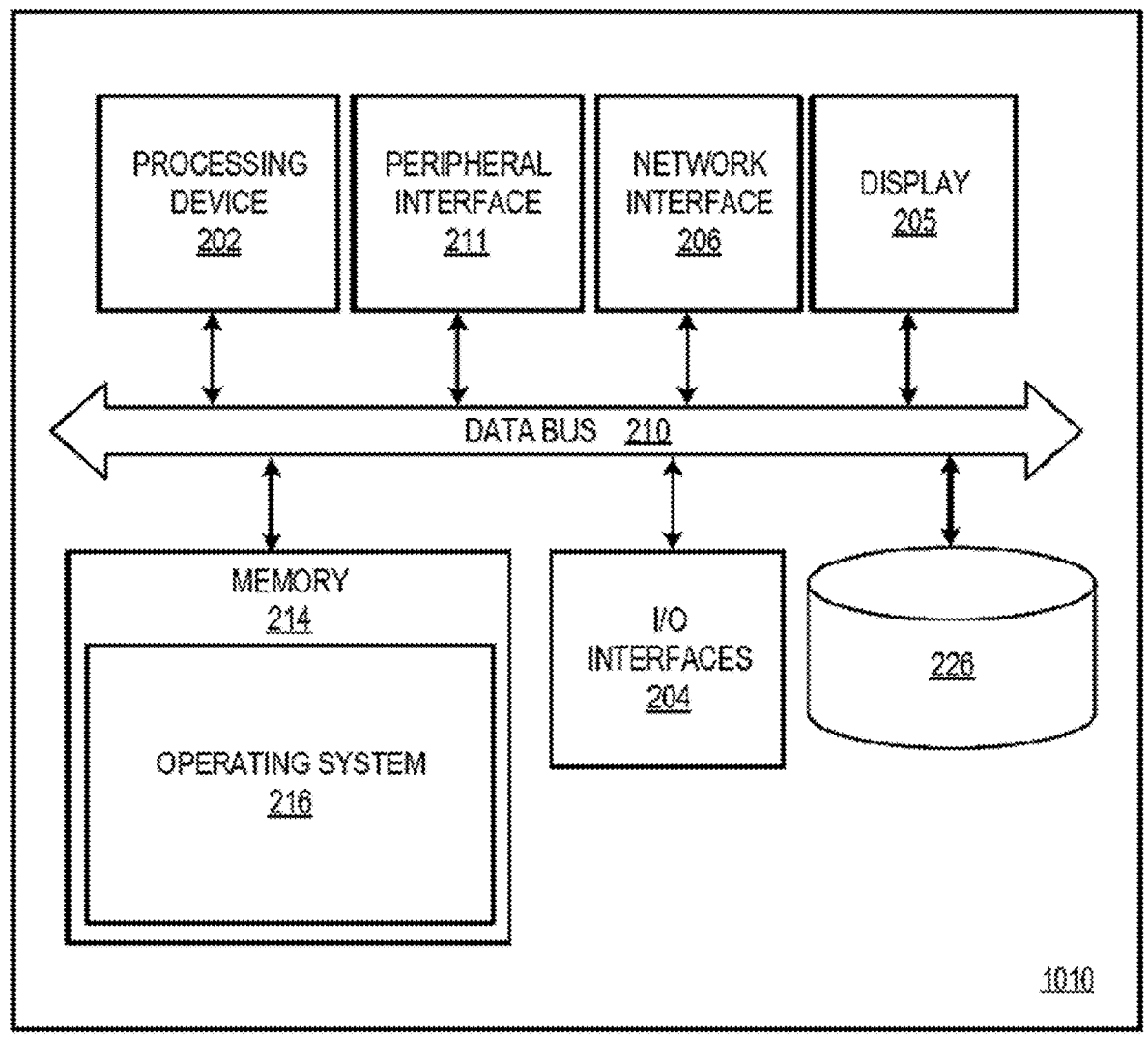
FIG. 14 shows an embodiment of a computing device or apparatus 1010 that can be implemented in the systems as described herein and which can implement methods as described herein.

Systems as described herein can be coupled to one or more computing devices to assist with automation of the system. FIG. 14, depicts an apparatus 1010 in which the devices, scanners, and methods as described herein may be coupled to in order to assist in automation of the system. The apparatus 1010 may be embodied in any one of a wide variety of wired and/or wireless computing devices, multi-processor computing device, and so forth. As shown in FIG. 14, the apparatus 1010 comprises memory 214, a processing device 202, a number of input/output interfaces 204, a network interface 206, a display 205, a peripheral interface 211, and mass storage 226, wherein each of these devices are connected across a local data bus 210. The apparatus 1010 may be coupled to one or more peripheral measurement devices (not shown) connected to the apparatus 1010 via the peripheral interface 211.

The processing device 202 may include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications may include application specific software which may be configured to perform some or all of the methods described herein. In accordance with such embodiments, the application specific software is stored in memory 214 and executed by the processing device 202. One of ordinary skill in the art will appreciate that the memory 214 can, and typically will, comprise other components which have been omitted for purposes of brevity.

Input/output interfaces 204 provide any number of interfaces for the input and output of data. For example, where the apparatus 1010 comprises a personal computer, these components may interface with one or more user input devices 204. The display 205 may comprise a computer monitor, a plasma screen for a PC, a liquid crystal display (LCD) on a hand held device, or other display device. Data from the scans, or images reconstructed from the imaging scans of the subject in the scanner (PET, EPRI, or both) can be outputted on the display for visualization.

In the context of this disclosure, a non-transitory computer-readable medium stores programs for use by or in connection with an instruction execution system, apparatus, or device. More specific examples of a computer-readable medium may include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 14, network interface device 206 comprises various components used to transmit and/or receive data over a network environment. For example, the network interface 206 may include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 may communicate with one or more computing devices via the network interface 206 over a network. The apparatus 1010 may further comprise mass storage 226. The peripheral 211 interface supports various interfaces including, but not limited to IEEE-1394 High Performance Serial Bus (Firewire), USB, thunderbolt, a serial connection, and a parallel connection.

Also described herein are methods of using systems as described herein. Also described herein are methods of combined PET-EPRI imaging or a subject, or methods of using a combined PET-EPRI system as described herein. The subject can be a mammalian subject (for example, without intending to be limiting, mouse, rat, pig, human) with a tumor.

In embodiments according to the present disclosure, methods as described herein can comprise: providing the subject; positioning the subject in a subject module of a combined PET-EPRI imaging scanner; and imaging a region of interest (ROI) of the subject with the scanner. In embodiments of the present disclosure, the region of interest of a subject can be a tumor. In embodiments of the present disclosure, the region of interest of a subject can be a microenvironment of a tumor.

Methods as described herein can further comprise administering to the subject a PET probe, an EPRI probe, or both. Without intending to be limiting, in certain aspects, the PET probe can be fludeoxyglucose (also known as flurodeoxy-glucose or 18F-fluorodeoxyglucose (18F-FDG)). Without intending to be limiting, in certain aspects, the EPRI probe can be a trityl radical, such as phosphonated triarylmethyl radicals (pTAM).

In embodiments of the present disclosure, imaging the ROI of the subject can comprise collecting PET data from the ROI of the subject with the imaging scanner, EPRI data from ROI of the subject with the imaging scanner, or both.

In embodiments of the present disclosure, imaging can further comprise reconstructing an image of the PET scan from the PET data, an image of the EPRI scan from the EPRI data, or both.

In embodiments according to the present disclosure, methods as described herein can further comprise overlaying the image of the PET scan and image of the EPRI scan.

In embodiments according to the present disclosure, methods as described herein can further comprise monitoring physiological parameters of the subject before, during, or after the imaging, individually or in combination.

In embodiments according to the present disclosure, methods as described herein can further comprise modulating the temperature of the subject module. In embodiments according to the present disclosure, methods as described herein can further comprise modulating the temperature of the subject in the subject module subject module. While embodiments of the present disclosure are described in connection with the Examples below and the corresponding text and figures, there is no intent to limit the invention to the embodiments in these descriptions. On the contrary, the intent is to cover all alternatives, modifications, and equivalents included within the spirit and scope of embodiments of the present disclosure.

EXAMPLES

Example 1

Objectives:

Electron paramagnetic resonance (EPR) enables interrogation of electron spins of free radicals to detect relatively stable compounds. EPR-based techniques in combination with paramagnetic contrast agents are accurate methods for measuring characteristics of the extracellular physiologic environment (oxygen saturation and pH, for example). Whereas, PET imaging is used mostly to interrogate intracellular physiology (glucose metabolism and amino acid incorporation, for example). The combination of these two methods has the potential to enable unique investigations studying the dynamics between cellular physiology and tissue microenvironment. An objective in this investigation is to explore the interactions between PET and EPR systems when they are combined in to a single scanner.

Figure 3B:
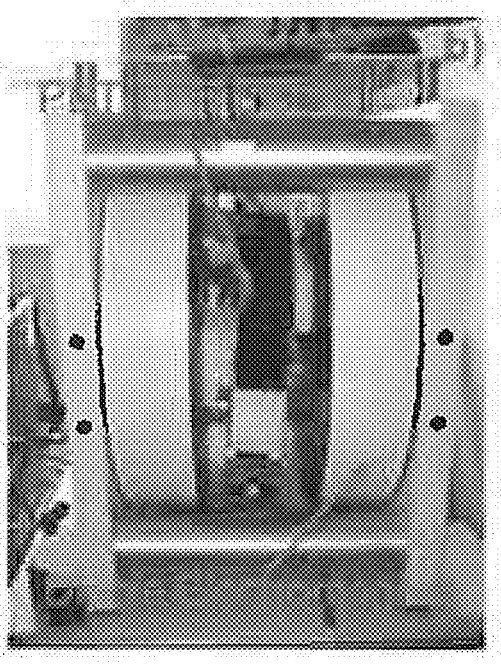
FIG. 3B is a photograph depicting an embodiment of a PET-EPR insert in an embodiment of an electromagnet.

Methods:

The PET scanner used in this study is a portable ring of twelve detector modules, each comprising of an array of LYSO detector elements (1.5 mm×1.5 mm×10 mm) coupled to an array of SiPMs. The EPR system is comprised of a dipole electromagnet (field strength up to 400 G), an RF bridge/resonator (resonant frequency=750-850 MHz) and a rapid scan (RS coil) magnetic field modulation unit (comprising a frequency generator to provide the voltage signals driving the coils, operating at up to 100 kHz and peak-to-peak field modulation=40 G) (FIG. 3A). The RS coil and resonator were mounted inside the bore (also described herein as the inner diameter) of the PET scanner (FIG. 3A). The combined system was then inserted into the magnet (FIG. 3B). A 3 ml sample solution containing a mixture of EPR contrast agent (3 mM water solution of stable trityl radical) and 7OuCi of FDG was placed in a conical vial and positioned at the center of the PET-EPR scanner. Simultaneous PET image data and EPR spectra were then acquired.

Figure 3C:
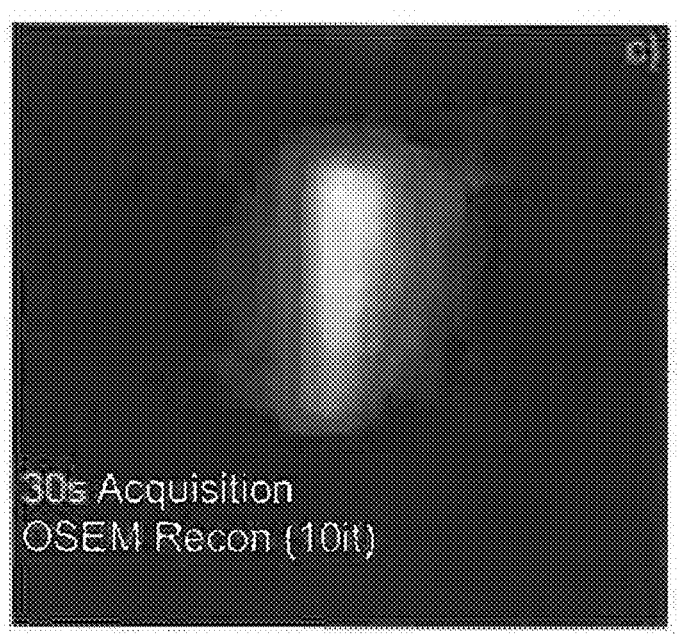
FIG. 3C is a PET image of a conical vial containing PET-EPR phantom solution.
Figure 3D:
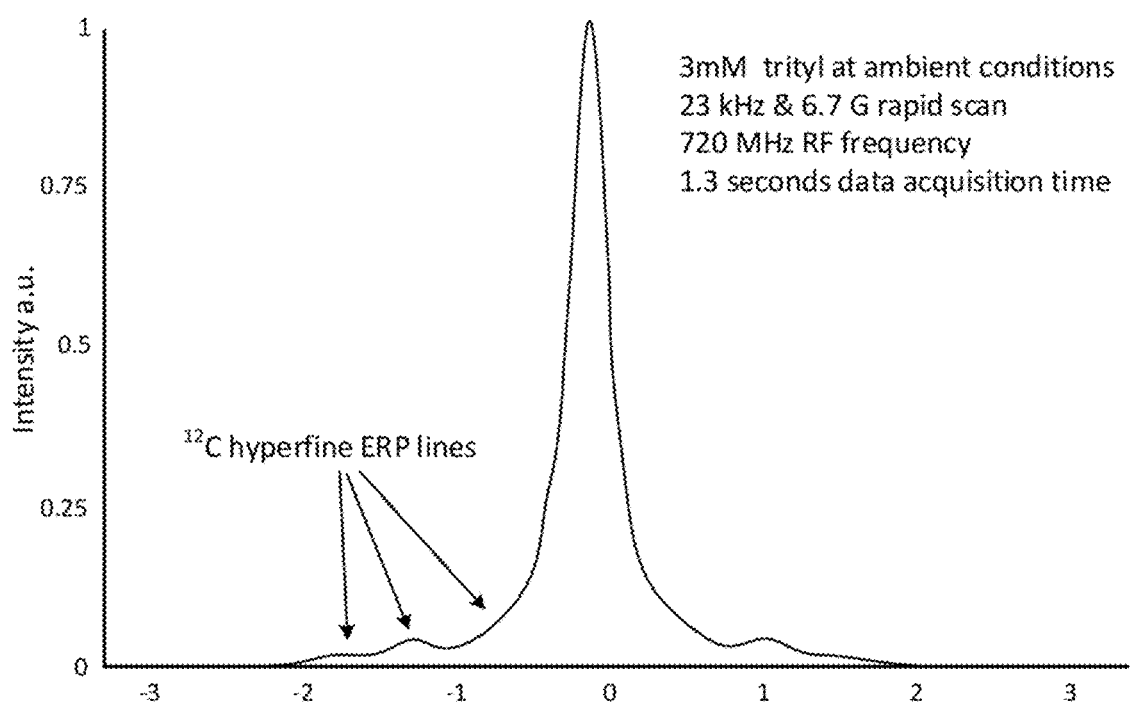
FIG. 3D is a rapid scan EPR spectrum of the phantom solution from the conical vial above.

Results:

PET energy and EPR spectra acquired during the scan showed no effects from simultaneous operation of the systems. Specifically, no artifacts or energy shifts were apparent in the PET spectra (FIG. 3C). Likewise, the EPR spectra demonstrated no apparent artifacts or anomalous source of noise from the operation of the PET scanner (FIG. 3D). PET images and EPR spectra of the combined PET-EPR tracer also showed no apparent artifacts.

Conclusion:

A combined PET-EPR system has the promise to enable unique and potentially important studies exploring the relationship between intracellular function and the extracellular microenvironment in cancer and cardiac tissues, potentially leading to new insights into the physiologic dynamics of these cells. This initial investigation demonstrated that there are no significant impediments to the melding of these two techniques. Additional modifications to the system, such as adding gradient coils to the EPR system to permit imaging, and modification of the PET scanner to increase imaging performance (resolution and detection sensitivity) by changing the scanner form to an annular scanner, for example, can also be undertaken.

Example 2

Figure 6:
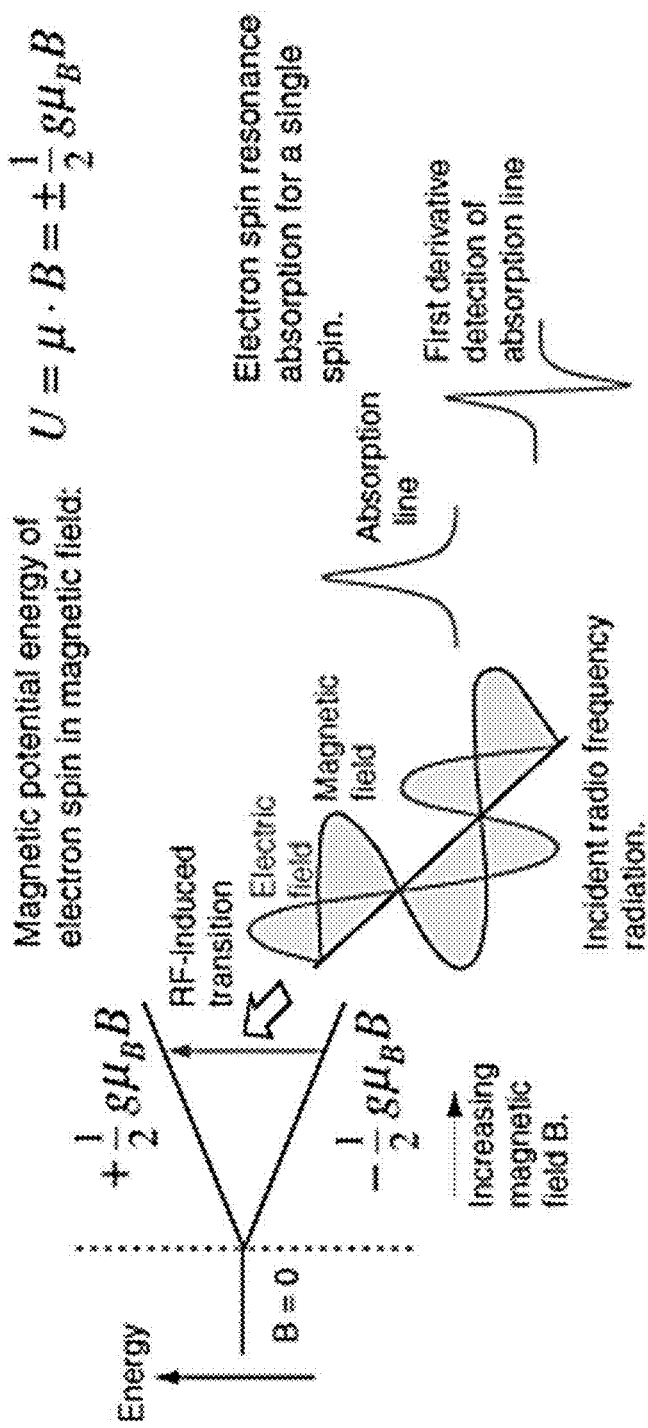
FIG. 6 illustrates principals underlying EPR spectroscopy and imaging.

EPR enables interrogation of electron spins in free radicals to detect relatively stable compounds (principals illustrated in FIG. 6). This technique, in combination with paramagnetic probes, is an accurate method for measuring mostly extracellular physiologic parameters (ie. pH, phosphate concentrations and $pO_2$). PET utilizes radiopharmaceuticals to quantify mostly intracellular parameters (ie. glucose metabolism).

Thus, there is an opportunity to simultaneously measure the relationship/interaction between intra- and extracellular components of tissue dynamics, which could provide unique perspectives of a number of tissue systems (ie. tumor and cardiac microenvironments).

EPRI is originally a spectroscopic technique. It utilizes lower magnetic fields than MR (~280 G) and high RF frequencies (>250 Mhz). Recently, this method has been adapted to acquire images through the application of gradient magnetic fields. It is often used in conjunction with externally-applied probes (tracers) whose EPR spectra can be used to measure physiologic properties (pH, phosphate concentrations, and $pO_2$, for example).

As shown in FIG. 4, a PET-EPRI insert was developed for use within a scanner which can utilize PET imaging, EPR imaging, and both modalities in combination. The insert comprised both a PET component and an EPRI insert. The PET component of the insert comprised a ring of twelve detector modules (diameter=20 cm), each comprising an array of lutetium-yttrium oxyorthosilicate (LYSO) detector elements (1.5×1.5×10 mm$^3$) coupled to an array of silicon photomultipliers (SiPMs, 4ch multiplexed readouts).

The EPR component comprised a dipole electromagnet (280 G), the RF bridge/resonator described above and the RS-coil (operating at up to 100 kHz and peak-to-peak field modulation=40 G).

Figure 5A:
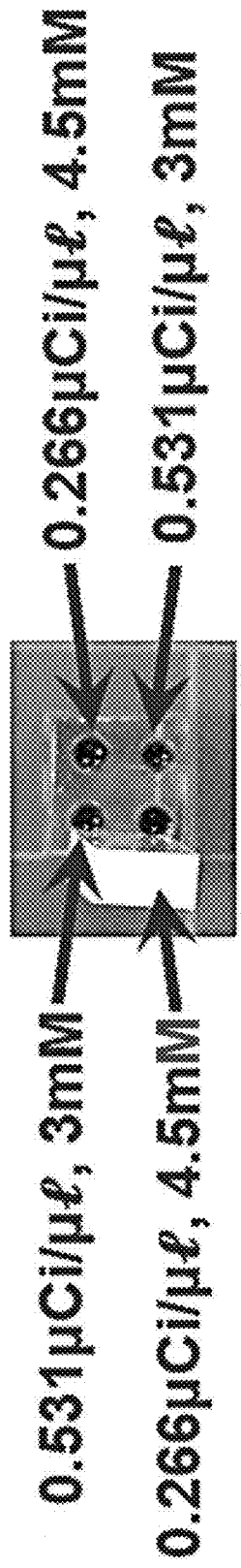
FIG. 5A is a photography of a dual modality phantom comprising a 2×2 array of 2 mm diameter cylinders (7 mm long). The cylinders can be filled with a mixture of FDG and trityl compound (with an oxygen sensitive radical for EPR).
Figure 5B:
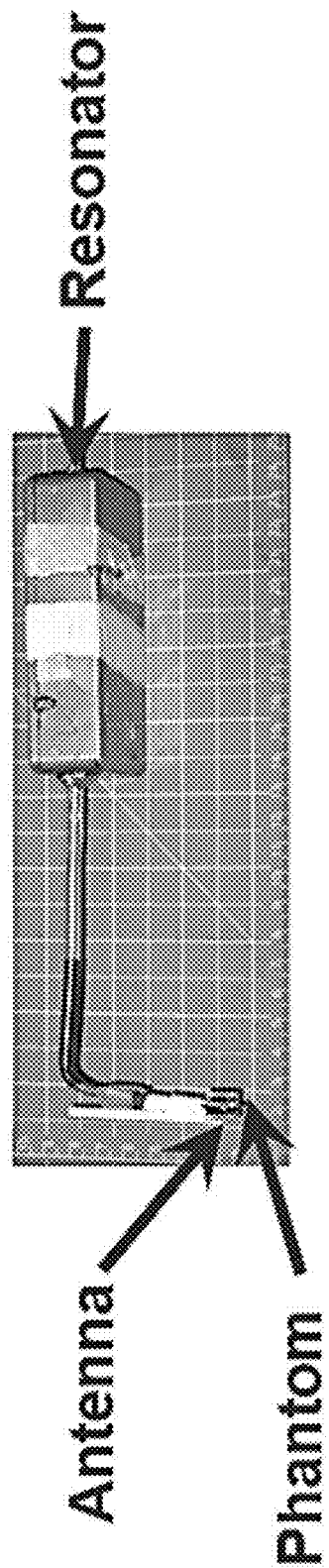
FIG. 5B is a photograph depicting in an embodiment the phantom positioned in relation to an embodiment of a resonator and an antenna.
Figure 5C:
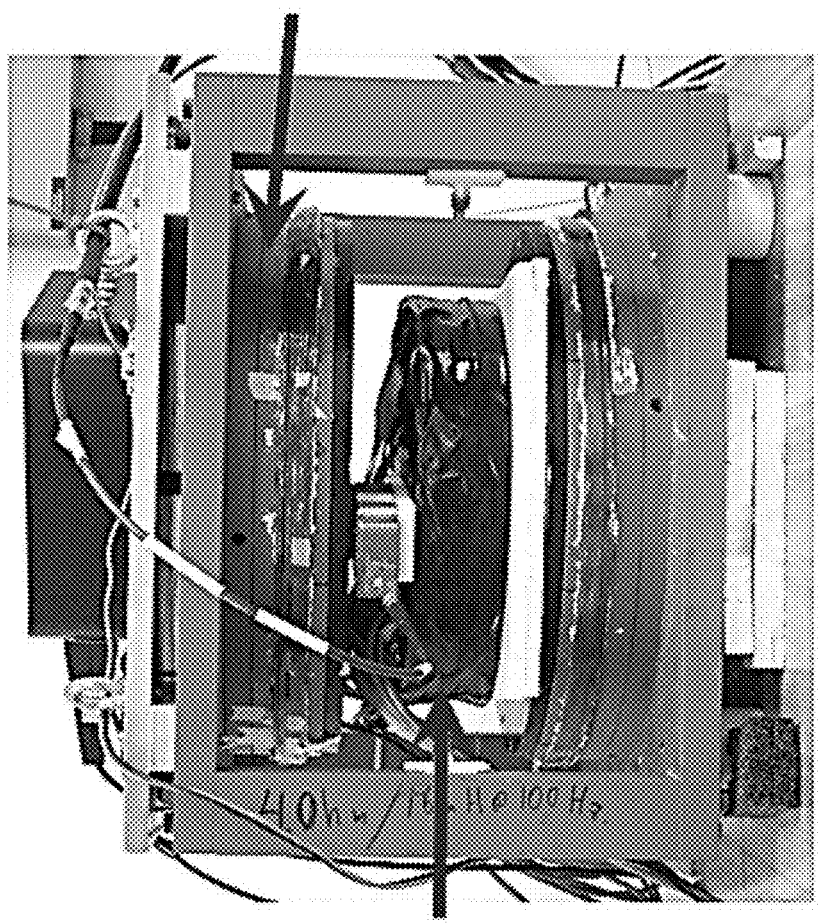
FIG. 5C shows a photograph of an embodiment of an insert placed in a dipole magnet.

To test the apparatus, a phantom was used as shown in FIG. 5A. The phantom was a dual modality phantom comprising a 2×2 array of 2 mm diameter cylinders (7 mm long). The cylinders were filled with a mixture of fluorodeoxyglucose (FDG) and trityl compound (oxygen sensitive radical for EPR). The phantom was placed in the resonator (FIG. 5B) and then in the center of the PET-EPR insert. The insert was then placed in the magnet (FIG. 5C) and simultaneous PET-EPRI acquisition was performed for 10 min.

Figures 7A, 7B, 7C:
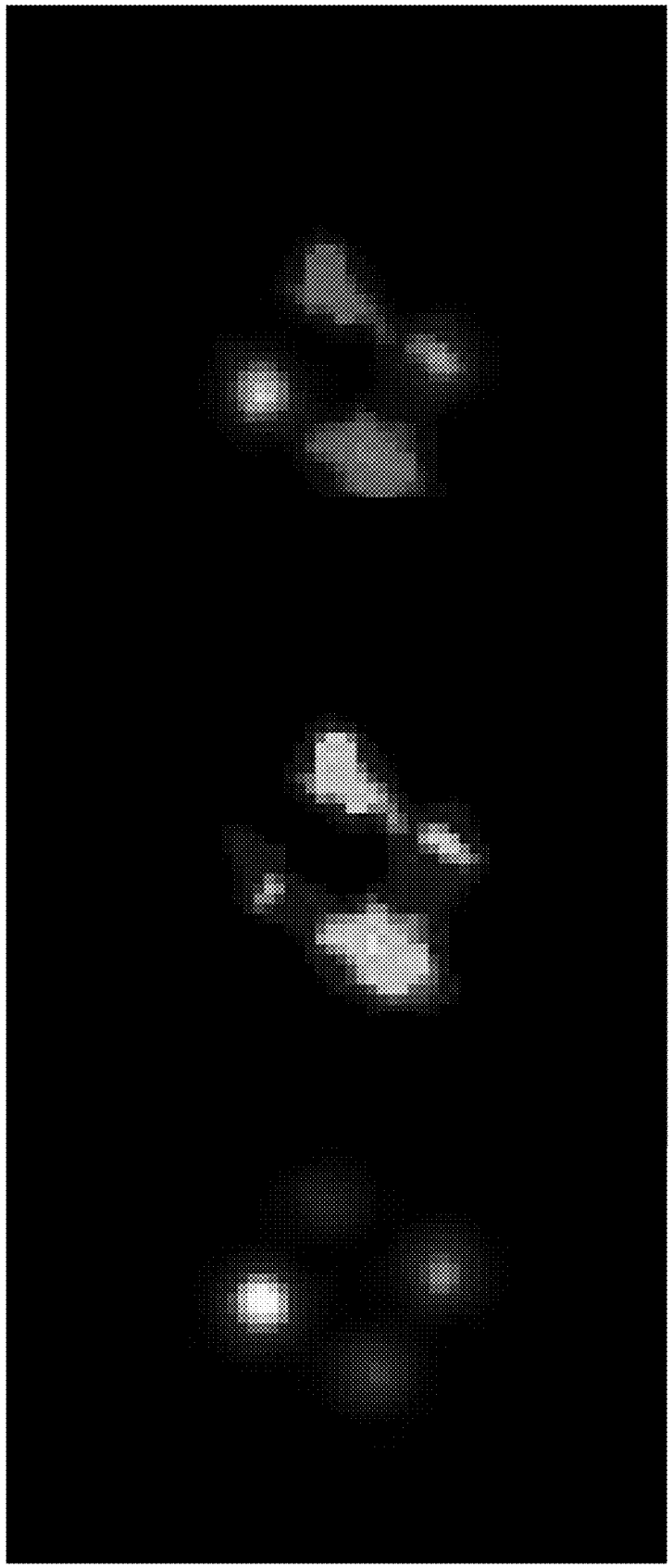
FIGS. 7A-7C show scanning results from the phantom of FIG. 5A and an embodiment of a PET-EPRI scanner as described herein.

The results of the phantom scan using the PET-EPRI scanner are shown in FIGS. 7A-7C. FIG. 7A shows the EPRI results, FIG. 7B shows the PET results, and FIG. 7C shows the combined PET/EPRI results. As shown in the figures, all four cylinders were visualized by both PET and EPR scanners of the insert. The relative intensities of FDG and trityl concentrations based on observed image intensities were consistent with and correlated with the actual concentrations. EPRI recovered H:L ratio and PET underestimated H:L ratio (noise) and there were no image artifacts.

Example 2

Data Acquisition Electronics

Figure 8:
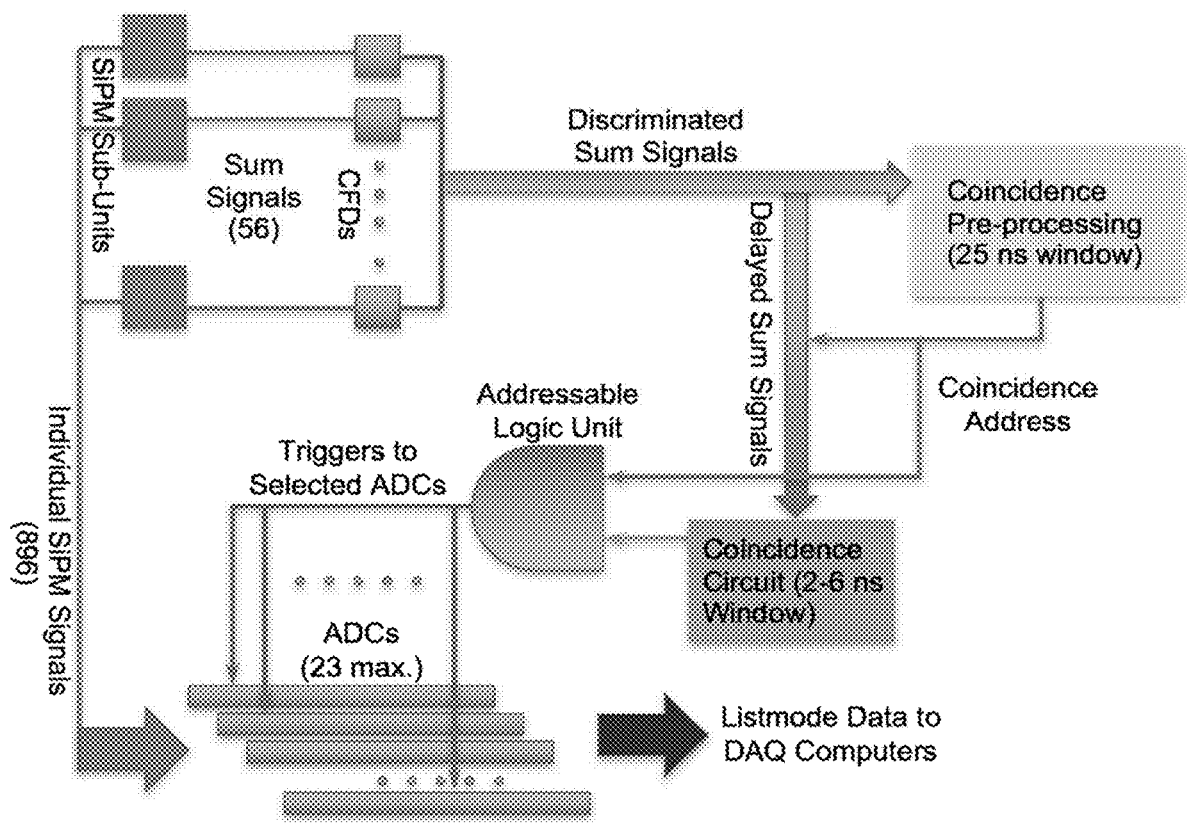
FIG. 8 shows an embodiment of data acquisition electronics that can be implemented into systems and methods as described herein.

To enhance the efficiency of the data acquisition (DAQ) system, a novel, flexible zone event triggering system can be used (see FIG. 8). Specifically, the sum outputs from individual SiPM sub-units can be grouped into user selectable-sized zones whose position is flexible. Specifically, the electronics can identify the position of the maximum SiPM sum signal. Signals from adjacent sub-units can then be summed (the number of sub-units to be included will be selectable). Based on preliminary studies, signals from the four sub-units adjoining the primary sub-unit can sample an average of 83% of the scintillation light produced by each event, so this trigger zone size can be used and assessed. The sum of the amplitude signals from the grouped sub-units can be representative of the energy deposited in the scintillator. These signals can be amplitude-discriminated (threshold will be adjustable, nominally 350 keV) and then divided into two data streams: one set of signals delayed and routed to an addressable switching unit, the other to a coincidence pre-processor. The coincidence pre-processor can be based on a Xilinx complex programmable logic device (CPLD). The pre-processor will form the trigger zones using the discriminated sub-unit outputs. It will implement a bi-signal programmed matrix coincidence logic scheme with a relatively wide timing window (25-30 ns). Apart from producing a TTL coincidence signal upon determination of a coincidence, it can set a position register containing the addresses of the sub-units involved in the coincidence. This information can be used by an addressable switching unit to route the appropriate delayed sum signals to a coincidence unit for final determination of a coincidence (selectable coincidence window, nominally 6 ns). The coincidence pre-processor unit can make it possible to determine the identities of the detectors involved in the coincidence and reduces the number of non-coincidence events that are processed by the full set of trigger electronics. Thus, the number of events processed by the coincidence unit can be limited, reducing dead time and maximizing count rate efficiency. If a coincidence is detected, the addressable logic unit can distribute the trigger pulses to the appropriate ADCs (determined by the CLPD-supplied addresses) for digitization of the individual analog SiPM signals. The digitized data can be routed to a series of networked CPUs, where the event's x- and y-coordinate as well as its DOI and energy can be identified using calculations performed on the signals, in tandem with previously measured calibration maps.

The x- and y-coordinates can be calculated from the digitized outputs by determining the 2D-center-of-mass of the scintillation light distribution recorded by the SiPMs. The z-coordinates (equivalent to DOI) can be estimated by taking a ratio of the total number of counts in the photon distribution (calculated by the DAQ trigger electronics) to its peak intensity (N/I). Note that non-uniformities of light output in the scintillator (specified to be approximately ±1.5%), which could affect the calculation of DOI, can be normalized via the N/I ratio method used to estimate event depth.

Example 3

The advent of hybrid scanners, combining complementary modalities, has revolutionized the application of advanced imaging technology to clinical practice and biomedical research. The melding of two complementary, functional imaging methods is described herein: positron emission tomography (PET) and electron paramagnetic resonance imaging (EPRI). PET radiotracers can provide important information about cellular parameters, such as glucose metabolism. While EPR probes can provide assessment of tissue microenvironment, measuring oxygenation and pH, for example. Therefore, a combined PET/EPRI scanner can provide new insights not attainable with current imagers by simultaneous acquisition of multiple components of tissue microenvironments. To explore the simultaneous acquisition of PET and EPR images, an embodiment of a prototype system was created by combining two existing scanners. Specifically, an embodiment of a silicon photomultiplier (SiPM)-based PET scanner ring designed as a portable scanner was combined with an embodiment of an EPRI scanner designed for the imaging of small animals. The ability of the system to obtain simultaneous images was assessed with a small phantom comprising four cylinders containing both a PET tracer and EPR spin probe. The resulting images demonstrated the ability to obtain contemporaneous PET and EPR images without cross-modality interference.

Adaptation of advanced clinical imaging methods for use with small animals transformed translational research. No longer are large numbers of animals necessary to perform many biomedical experiments. Many small animal scanners combine an anatomical imaging modality (magnetic resonance imaging (MRI) or x-ray computed tomography (CT), for example) with a complementary functional imaging method (positron emission tomography (PET) or optical imaging, for example). The combination of two complementary, functional imaging methods is described herein: PET and electron paramagnetic resonance imaging (EPRI).

PET can utilize administration of pico-molar concentrations of positron-emitting radiotracers and can be used to measure numerous physiologic parameters such as glycolysis rates, DNA synthesis, and cell replication rates. EPRI can enable interrogation of electron spins in free radicals that, when used in combination with paramagnetic probes, can be an accurate method for quantifying components of tissue microenvironments. Triarylmethyl radicals are promising probes that possess very good stability, long relaxation times, and narrow line widths (enhancing sensitivity and spatial resolution). EPR probes can be used to investigate extracellular or intracellular components of tissue microenvironments, such as $pO_2$, pH, and phosphate concentration (Pi). These parameters can be important because they characterize tissue microenvironments in pathological conditions such as cancer and heart disease.

Combination of PET and EPRI, can enable simultaneous measurement of important intra- and extracellular components of tissue microenvironments (glucose consumption rate, hypoxia and acidosis, for example). Thus, a pre-clinical PET/EPRI scanner can be a powerful tool for performing novel, in vivo, investigations of biological systems, leading to insights that can be translated into improved understanding of normal physiology, and methods for enhancing diagnosis and treatments of diseases. It can be important that the PET and EPRI data are acquired as temporally aligned as possible since the biochemical milieu of an animal is not static. Physiological parameters, such as glucose metabolism, pH, Pi, and $pO_2$ levels may vary over short time periods (minutes to tens of minutes). Therefore, to ensure accurate, synchronized, and unbiased measurements of interactions among components of physiology, it can be important to perform simultaneous imaging to capture their correlated temporal evolution. Simultaneous scanning also can facilitate accurate measurement of complex physiological responses to controlled administration of a chemical stimulus that momentarily perturbs the animal's biochemistry. Additionally, the combination of both systems into a single unit can simplify the co-registration process, since both scanners share a coordinate system. Finally, simultaneous scanning can increase the efficiency of the imaging process, which is can be important if many animals must be scanned in a short amount of time. Described herein is the construction of and testing of an embodiment of a preclinical PET/EPRI scanner.

The embodiment of the PET scanner used in this study was constructed at West Virginia University as part of a continuing effort to produce images of the brains of ambulatory subjects. As described herein, an embodiment of a PET scanner can comprise a ring of twelve detector modules (inner diameter=21 cm). Each module contains a 32×32 array of polished LYSO detector elements (1.5 mm×1.5 mm×10 mm), separated by 0.07 mm thick ESR reflector (Proteus, Chagrin Falls, Ohio). The twelve scintillation blocks can be individually coupled to 10×10 arrays of 3 mm×3 mm (4.85 mm pitch) S10362-series MPPCs (multi-pixel photon counters) (Hamamatsu Photonics, Shizuoka, Japan). The MPPCs can be readout with multiplexed, 4ch-readout electronics (AiT Instruments, Newport News Va.). The forty-eight amplified analog signals can be digitized with an FPGA-based, 64-channel data acquisition module (AiT Instruments, Newport News, Va.) (Proffitt et al 2005, 2006). Digitization can be initiated by a TTL signal generated by a sixteen channel, Mesytec MCFD-16 NIM module (Mesytec, Putzbrunn GmbH, Germany) (coincidence window=10 ns) that can determine coincidences between any two of the twelve detectors in the ring. Data acquisition can be performed using Java programming language-based software (McKisson et al 2007) with a user interface created with the Kmax scientific programming package from Sparrow Corp. (Port Orange, Fla.).

For each coincident event, the identification of the detector elements struck by the annihilation photons can be determined by performing center-of-mass calculations on the digitized light distributions detected by the MPPCs in conjunction with a previously measured calibration file mapping event position to detector element number. The amount of energy deposited by each photon in the scintillator can be determined by converting the sum of the analog signals to energy with the aid of a pre-measured calibration table. The position and energy information is then stored in list mode format. These data can be used to create 3D maps of radiotracer distribution with the MLEM (Maximum-Likelihood Expectation-Maximization) iterative reconstruction algorithm (as described in Smith M F, Raylman R R, Majewski S and Weisenberger A G 2004 Positron emission mammography with tomographic acquisition using dual planar detectors: initial evaluations Phys. Med. Biol. 49 2437-52, which is incorporated by reference herein in its entirety). The nominal image voxel size can be 1.0 mm×1.0 mm×1.0 mm. The spatial resolution of the system can be 2.2 mm (full width-at-half-maximum (FWHM) 5 mm from center of scanner); peak detection sensitivity is 0.5%. The average timing resolution of the PET modules can be 2.1 ns FWHM; note that the system does not have time-of-flight capabilities. More details of the PET scanners, and this embodiment, as described herein are described in Bauer C, Stolin A, Proffitt J, Martone P, Brefczynski-Lewis J, Lewis J, Hankiewicz J, Raylman R and Majewski S 2013 Development of a ring PET insert for MRI *IEEE Nuclear Science Symp. Conf. Record* vol 9 pp 101-8, which is fully incorporated by reference in its entirety herein.

An embodiment of the EPR imager as described herein was constructed at West Virginia University as part of an ongoing effort to explore and advance EPRI methodology. It utilizes the recently developed rapid scan (RS) EPR technique (RS-EPR) (as described in Biller J R, Tseitlin M, Mitchell D G, Yu Z, Buchanan L A, Elajaili H, Rosen G M, Kao J P, Eaton S S and Eaton G R 2015 Improved sensitivity for imaging spin trapped hydroxyl radical at 250 MHz ChemPhysChem 16 528-31; Elajaili H B, Biller J R, Tseitlin M, Dhimitruka I, Khramtsov V V, Eaton S S and Eaton G R 2015 Electron spin relaxation times and rapid scan EPR imaging of pH-sensitive amino-substituted trityl radicals Magn. Reson. Chem. 53 280-4; Epel B, Sundramoorthy S V, Krzykawska-Serda M, Maggio M C, Tseytlin M, Eaton G R, Eaton S S, Rosen G M, Kao J P Y and Halpern H J 2017b Imaging thiol redox status in murine tumors in vivo with rapid-scan electron paramagnetic resonance J. Magn. Reson. 276 31-6; Moser J, Lips K, Tseytlin M, Eaton G R, Eaton S S and Schnegg A 2017 Using rapid-scan EPR to improve the detection limit of quantitative EPR by more than one order of magnitude J. Magn. Reson. 281 17-25; and Tseytlin M 2017 Full cycle rapid scan EPR deconvolution algorithm J. Magn. Reson. 281 272-8, the entirety of all of which are incorporated fully by reference herein). RS-EPR can improve signal-to-noise ratios of the measured spectra compared to the standard field-modulated, first-derivative method. Perhaps more importantly, it can permit acquisition of many projections in a short amount of time. The RS-coil which can acquire these data comprises two, 100-turn coils of Litz wire (separated by 7 cm) wound on a 14 cm-diameter, 3D-printed Polylactic acid (PLA) hollow cylinder (wall thickness=2 mm) to form a Helmholtz coil.

Figure 9:
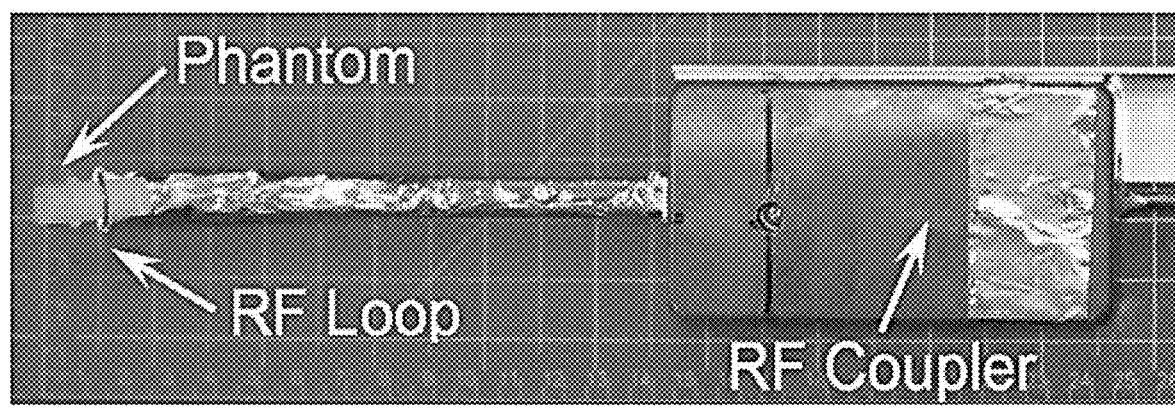
FIG. 9 is a photo of an embodiment of the surface coil resonator (RF surface loop and RF coupler) and phantom.

The embodiment of the EPRI configuration used for co-imaging with the PET system described herein is similar to one previously described by Tseytlin et al (Tseytlin M 2017 Full cycle rapid scan EPR deconvolution algorithm J. Magn. Reson. 281 272-8, which is incorporated by reference fully herein). The EPRI resonator unit, shown in FIG. 9, is based on the design described by Hirata et al (Hirata H, He G, Deng Y, Salikhov I, Petryakov S and Zweier J L 2008 A loop resonator for slice-selective in vivo EPR imaging in rats J. Magn. Reson. 190 124-34, which is fully incorporated by reference herein in its entirety). It can comprise an RF surface loop (into which the sample is placed) connected to a distributed capacitor network containing two 50 Ohm coaxial cables and a coupling unit that matches the resonance structure to the 50 Ohm transmission line. The unit also can contain a $\lambda/2$ balun. The constant magnetic field which produces the EPR signals can be supplied by a permanent dipole magnet (Ningbo Jansen NMR Technology, Co). It can have a pole to-pole gap of 12.5 cm and can produce a magnetic field of ~268 G corresponding to ~750 MHz for an EPR spin probe with a g-factor of ~2. Elements of a Helmholtz coil are mounted on the magnet poles to facilitate fine tuning of the magnetic field up to ~293 G (820 MHz). Due to interference from cell phone signals (~750 MHz), a frequency of 800 MHz was chosen for measurements. Three-dimensional locations of the spin probe can be encoded via application of spatially varying magnetic fields supplied by three sets of gradient coils. The maximum magnetic field gradient used in imaging can be 3 G cm-1. The system can be capable of sub-millimeter spatial resolution when narrow-line trityl spin probes are used.

The imager can be calibrated using standard procedures. Specifically, the RS width can be verified by measuring hyperfine lines of the trityl 'Finland' radical (as described in Bowman M K, Mailer C and Halpern H J 2005 The solution conformation of triarylmethyl radicals J. Magn. Reson. 172 254-67, which is fully incorporated by reference herein in its entirety). The gradients can be calibrated by imaging of point-like particles of lithium octa-n-butoxynaphthalocyanine (LiNC-Buo), which produce EPR signals, arrayed in a cubic grid separated by known distances along the x, y, and z axes (as described in Pandian R P, Parinandi N L, Ilangovan G, Zweier J L and Kuppusamy P 2003 Novel particulate spin probe for targeted determination of oxygen in cells and tissues Free Radic. Biol. Med. 35 1138-48, which is fully incorporated by reference herein in its entirety). These procedures can facilitate production of 3D maps of $pO_2$ and probe concentration based on the data acquired by the embodiment of the system as described herein.

The EPR spectra of the probe used in this investigation can have two components, Gaussian and Lorentzian. The width of the Lorentzian component (EPRI-Lw) can be extracted, for example, from the spectral data using a line fitting procedure (as described in Khramtsov V V, Bobko A A, Tseytlin M and Driesschaert B 2017 Exchange phenomena in the electron paramagnetic resonance spectra of the nitroxyl and trityl radicals: multifunctional spectroscopy and imaging of local chemical microenvironment Anal. Chem. 89 4758-71, which is fully incorporated by reference in its entirety herein); its value is related to the presence of oxygen, or other paramagnetic compounds. The integral of the EPR spectra intensity can be related to probe concentration (EPRI-Conc). Four-dimensional images (three spatial axes and one spectral) of EPRI-Lw and EPRI-Conc can be reconstructed using, for example, the iterative backprojection method (as described in Komarov D A and Hirata H 2017 Fast backprojection-based reconstruction of spectral-spatial EPR images from projections with the constant sweep of a magnetic field J. Magn. Reson. 281 44-50, which is fully incorporated by reference in its entirety herein). This technique can involve more computational time than the standard filtered back-projection method (1-2 h), but is less likely to produce image artifacts. The nominal EPRI image voxel size can be 0.25 mm×0.25 mm×0.25 mm.

Figure 10:
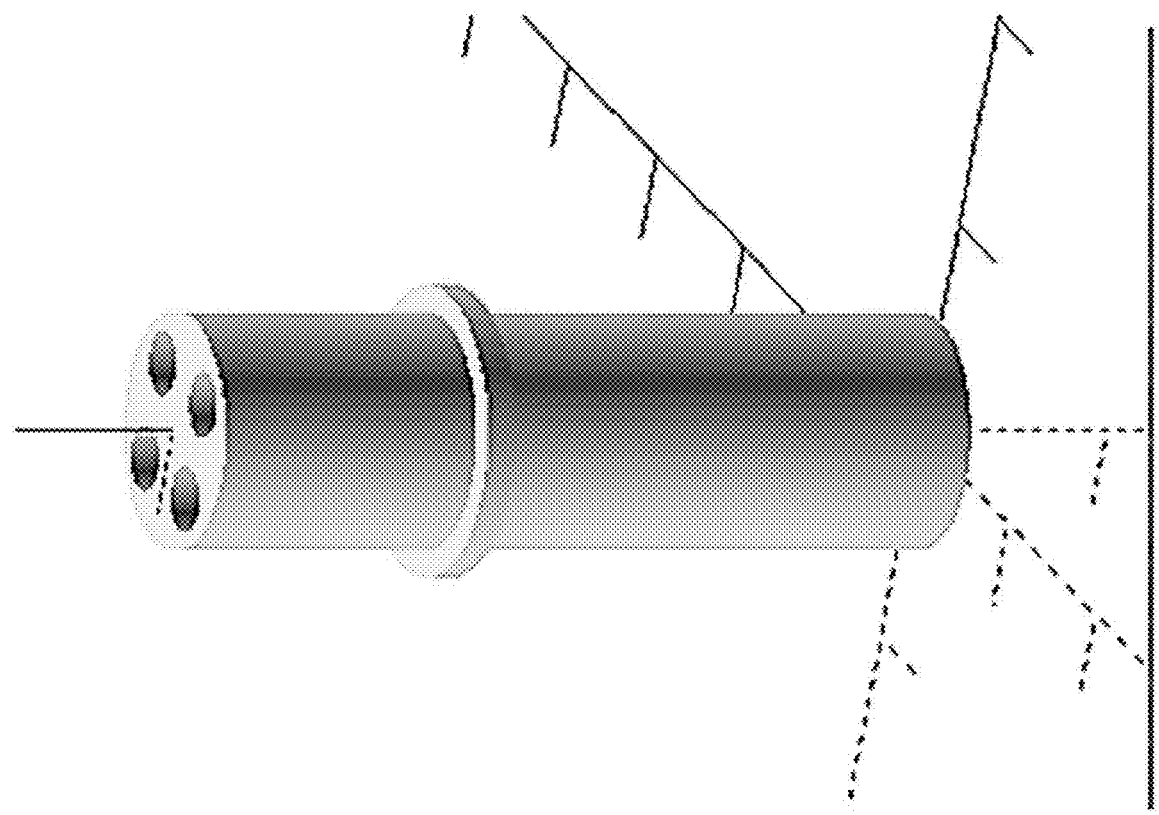
FIG. 10 is a mechanical drawing used to 3-D print and embodiment of the phantom.

To explore the capabilities of the PET/ERPI scanner, a multi-modality phantom was designed and fabricated with a FormLabs (Somerville, Mass. USA) Form2 3D printer. An embodiment of a digital model of the phantom is shown in FIG. 10. It has an outer diameter of 10.7 mm and contains four 254 µl cylinders (3 mm inner diameter; length=36 mm; center-to-center distance=4.6 mm). The cylinders were filled with specially-formulated, PET-EPR imaging solution. Specifically, an oxygen reporting spin probe, per-deuterated 'Finland' triarylmethyl (trityl) radical (dFT), was used to produce EPR signals. Since it can be difficult to accurately control oxygen concentration in the phantom, 1 mM of gadolinium contrast agent (Gd-DTPA, BioPAL, Worcester, Mass. USA) was added to 1 mM of dFT to emulate the presence of oxygen. Gadolinium shortens the relaxation times of the EPR probe by the same exchange interaction mechanism as oxygen. The PET radiotracer 18F-FDG was added to the EPR probe solution to create the dual-modality tracer.

Two variants of PET-EPRI imaging solution were created. One contained 1 mM of dFT, 1 mM of Gd and 25 µCi of FDG (defined as the $Gd^+F^-$ solution). The second contained 1 mM of dFT and 49 µCi of FDG (defined as the $Gd^0F^+$ solution). This concentration of dFT is comparable to that measured in vivo. Indigenous oxygen in the solutions was removed by adding glucose (10 mM, Sigma Aldrich, Cleveland, Ohio USA) and glucose oxidase (500 U ml$^{-1}$, Sigma Aldrich, Cleveland, Ohio USA). To make up the volume of the samples (254 µl), appropriate amounts of 0.1 M Na-phosphate buffer (pH=7.4) were added. The phantom was filled such that diagonally opposed cylinders contained the same solution type.

Figure 11:
FIG. 11 is a picture of an embodiment of a complete PET-EPRI system (PET scanner combined with the EPR resonator shown in FIG. 9). The orientation of the magnetic field, Bo, is shown.

To create the embodiment of the prototype PET/EPRI scanner, the PET detector ring was placed in the center of the dipole magnet (to permit access to the center of the PET scanner, it was tilted by approximately 20°) (FIG. 11). The EPR system's RS coils were placed in the center of the PET ring. The EPR RF loop holding the phantom (see FIG. 9) was inserted into the center of the PET-RS-coil combination. The orientation of the RF field is parallel to the axis of the loop. PET and EPRI data were obtained simultaneously (3 min scans). Images were created as described above. Following the PET-EPRI scan, the phantom was placed in a 1 T small animal ICON® MRI scanner (Bruker, Billerica, Mass. USA) (T1 FLASH; TR=41 ms; TE=4.8 ms; flip angle=30°; image voxel size=0.25 mm×0.25 mm×2.4 mm). Prior to registration, the MR, PET and EPR images underwent rigid body rotation and scaling based on their relative orientations and image pixel sizes. Registration was performed by overlaying the transformed images utilizing the Photoshop® image processing software (Adobe, San Jose, Calif. USA). Automated image registration software can also be used. While PET and EPRI can produce quantitative images, only qualitative comparisons between images from the modalities were done to simplify imaging processing. Thus, image intensities are utilized to represent relative radiotracer concentration, dFT probe concentration and simulated oxygen concentration.

Figures 12A, 12B:
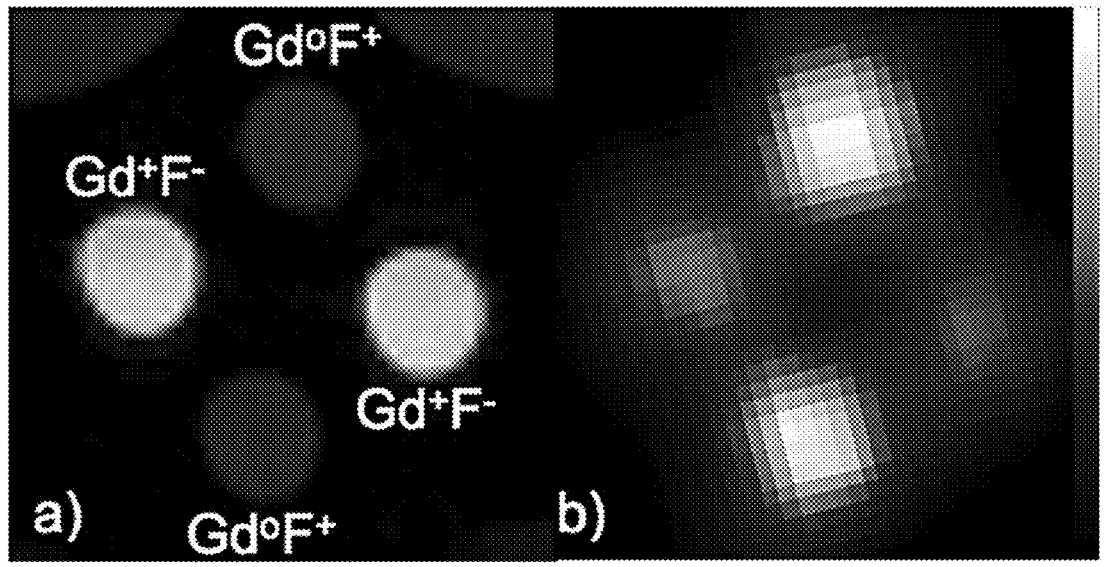
FIGS. 12A-12D depict PET-EPR images of the embodiment of the multi-mode phantom.
Figures 12C, 12D:
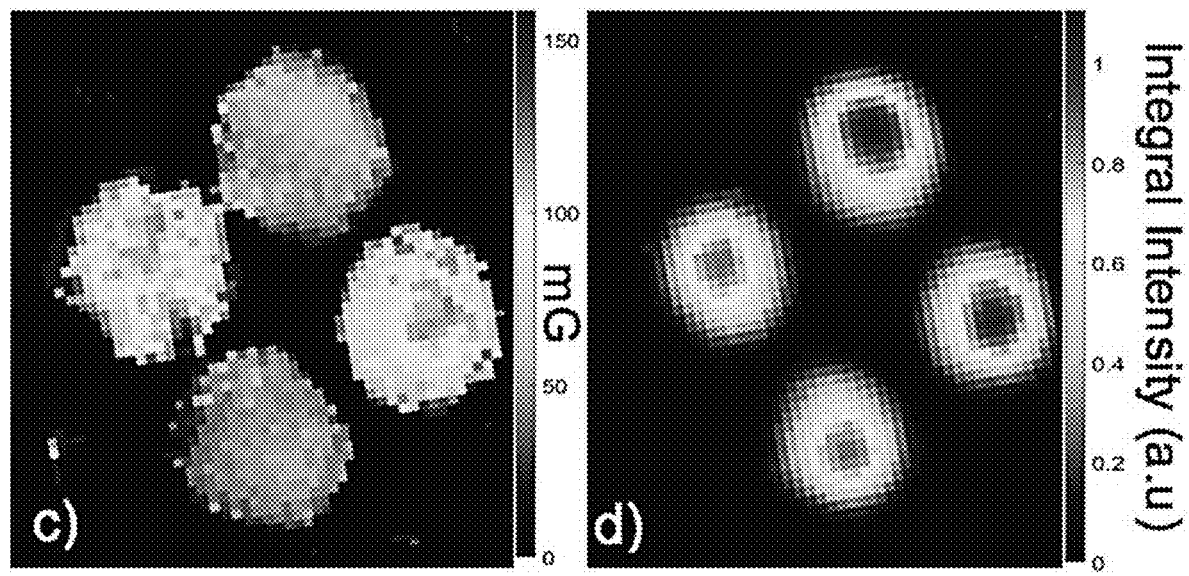
Figures 13A, 13B:
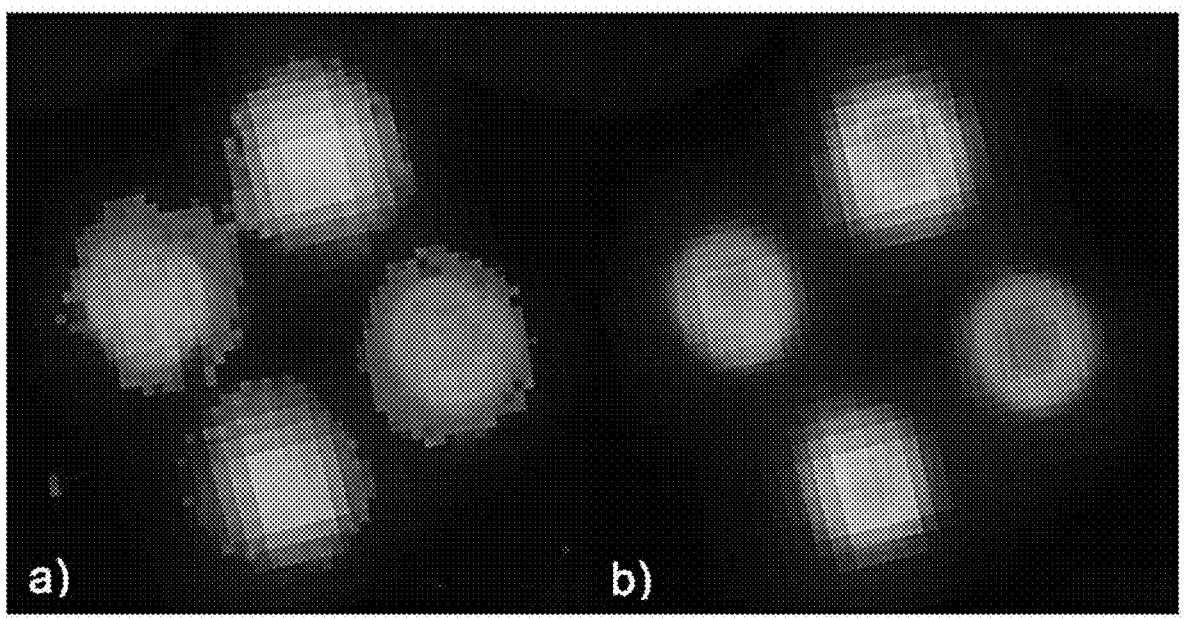
FIGS. 13A-13B are registered images combining MRI, PET, and EPRI-Lw (FIG. 13A) and MRI, PET, and EPRI-Conc (FIG. 13B).

FIG. 12A shows the T1-weighted MRI image of the phantom (the light gray semi-circles at the top corners are images of two small vials of water included with the phantom to facilitate tuning of the MRI scanner). The PET image in FIG. 12B illustrates the differences in FDG concentration of the two solutions based on relative image intensity. Importantly, there are no photon attenuation artifacts apparent in the images. FIG. 12C shows a map of the Lorentzian contribution to the EPR signal line width (EPRI-Lw), which is related to pO$_2$ in the sample (line width is measured in milli-Gauss). The image in FIG. 12D is a map of the intensity integral of the EPR spectra, which is related to the concentration of dFT in the solutions (EPRI-Conc). FIGS. 13A-13B shows registered PET, EPR (both modes) and MR images.

Combined PET and EPRI imaging has the potential to open new avenues of biomedical research. It could be used to explore various physiologically-important parameters of tissue microenvironments, potentially leading to novel insights into disease origins and progression. The results from the embodiment PET/EPRI scanner herein demonstrates the feasibility of performing simultaneous assessment of these parameters without any apparent cross-modality interference.

FIGS. 9-11 show the embodiments of the PET/EPRI system and phantom as described herein. Unlike other systems, such as the PET-Overhauser-MRI system described by Yamamoto et al (which may not be compatible with PET because of the RF power required), the PET scanner described herein is based on solid state-SiPM detectors. FIGS. 12A-12D illustrate the variety, and potential utility of images obtainable from a PET/EPRI scanner. Specifically, the PET image in FIG. 12B indicates the system's ability to map areas of positron-emitter by correctly identify the relative concentrations of FDG present in the cylinders based on image intensity. The resolution of the image may be somewhat compromised by the relatively low resolution of the PET scanner. The values of the spectral-line-width represented in the EPR images (EPRI-Lw) of the cylinders shown in FIG. 12C demonstrate the ability of the system to map oxygen concentration (simulated by the addition of Gd). Note that the cylinders that show the highest concentration of gadolinium (based on image intensity) correctly correspond to the cylinders with lowest FDG concentration ($Gd^+F^-$). This finding is compatible with MRI image (FIG. 12A). Specifically, the cylinders with higher MR signal correspond to the cylinders containing the gadolinium, which is an MR contrast agent. The probe-concentration-EPR image (EPRI-Conc) (FIG. 12D) shows, correctly, that there is little difference in probe concentration among the cylinders, based on their relative image intensities. The small intensity differences observed in this image can be due to the non-uniformity in resonator loop sensitivity as a function of position inside the loop. Thus, the images in FIGS. 12A-12D illustrate the ability of the system to simultaneously interrogate different functional properties reported by an EPR probe, in conjunction with assessment of PET tracer uptake.

There are no artifacts present in the PET and EPR images. This finding is likely due to the low static magnetic field (~285 G), relatively low strength magnetic gradients (3 G cm-1) and high frequency RF (800 MHz) used in EPRI, which are unlikely to result in interactions with the PET electronics or SiPMs. The lack of photon attenuation artifacts in the PET images can be due to the small size of the phantom and use of thin, low-density materials used in the construction of the RS-coils (the only component of the EPRI scanner in the PET scanner's field-of-view). Furthermore, there are no active elements of the PET scanner present inside the sensitive volume of the EPRI scanner, so the likelihood of PET-related effects on EPR images is significantly reduced. Finally, the ability to spatially, as well as temporally, correlate multiple parameters of tissue microenvironments, such as those assessed in this study is illustrated by the images shown in FIGS. 13A-13B.

The findings from this initial investigation showed that the combination of PET and EPRI is possible. As demonstrated herein, simultaneous data acquisitions facilitated the localization of complementary intra- and extra-cellular probes. PET/EPRI, therefore, could enable novel investigations exploring the dynamics of tissue microenvironments. Further embodiments of the system as described herein can comprise a compact, EPR-compatible PET system based on a monolithic annulus of scintillator (as described in Stolin A V, Martone P F, Jaliparthi G and Raylman R R 2017 Preclinical positron emission tomography scanner based on a monolithic annulus of scintillator: initial design study J. Med. Imaging 4 011007, which is fully incorporated by reference in its entirety herein) possessing higher resolution and detection sensitivity than other embodiments.

Example 4

A combined PET/EPRI scanner addresses an unmet need for the ability to perform temporally correlated measurements of the intra- and extracellular components of physiological microenvironments. Specifically, quantification of intracellular parameters with PET complements the ability of EPRI to quantify extracellular parameters. Insights gained from measurements made with this system could result in development of new methods for disease prevention, diagnosis and treatment. While embodiments of PET/EPRI scanners described herein are designed for use in mice, it is not intended to be limited to such as would be noted by the skilled artisan.

It should be noted that PET-EPR imaging could be performed by sequentially scanning animals on separate systems (like the methodology used to combine fMRI and EPRI). This process, however, requires transport of the animals between two scanners, resulting in a time delay between measurements. The biochemical milieu of anesthetized mice, however, is not static; physiological parameters, such as glucose metabolism, pH, Pi and $pO_2$ levels may vary over short time periods (minutes to tens of minutes). Therefore, to ensure accurate, synchronized and unbiased measurements of interactions among components of physiology, it can be important to perform simultaneous imaging to capture and correlated their temporal evolution. For example, if glucose metabolism rate, $pO_2$ and/or pH of the tissues change during the scanning time, this evolution will be captured on a similar time scale by both systems only if scanning is performed simultaneously (as demonstrated by simultaneous PET-MRI studies previously). Simultaneous scanning also can facilitate accurate measurement of complex physiological responses to controlled administration of a chemical stimulus (breathing of carbogen, for example) that momentarily perturbs the animal's biochemistry. The combination of both systems into a single unit, also simplifies the registration process, since both scanners share a coordinate system. Finally, simultaneous scanning greatly increases the efficiency of the imaging process, which is important if many animals must be scanned in a short amount of time.

An example of the type of study possible with a PET/EPRI scanner is investigation of the possibility of progression to carcinogenesis is a somatic evolutionary process, similar in some ways to Darwinian evolution. The pre-malignant extracellular environment is often hypoxic, favoring neoplastic cells that exhibit increased glycolysis and hence glucose transport (overexpression of the GLUT-1 transporter) (the Warburg effect). This process results in reduced pH of the tumor microenvironment (TME) since glycolysis produces acidic byproducts. The acidic environment exerts selection pressure on cells to develop resistance to apoptosis and upregulation of membrane $H^+$ transporters to maintain intracellular pH. As the tumor grows, angiogenesis progresses and $pO_2$ changes. The cells, however, continue to utilize glycolysis to produce energy. Ultimately, the increasingly acidic environment facilitates invasion of the neoplastic cells into adjacent tissues. A PET/EPRI scanner could provide a unique opportunity to observe this progression. Specifically, simultaneous, in vivo measurements of intracellular glycolysis rates (with FDG-PET, for example) and extracellular $pO_2$ and pH (with pTAM-EPRI) in a cohort of animals exhibiting spontaneous tumors could be made at numerous time points to explore the dynamic relationship between glycolysis and TME.

While a combined PET/EPRI scanner could permit novel and potentially important experiments to be performed, construction of the system can be challenging. Integration of the two modalities requires special considerations to minimize mutual interactions between the systems that can produce sub-standard performance. The individual scanners are designed such that their combination into a single unit will not compromise their performance. Cross-modality interference can be assessed using measurements performed with phantoms, before and after integration.

Integration of PET and EPRI as described herein has not previously been attempted. Development of the proposed system can be a unique challenge, requiring innovative techniques to accomplish; it can appear and operate like no other hybrid scanner. The PET component can utilize a unique compact design to reduce interference with the EPRI scanner, enhance performance, and fit inside the confined space of the EPRI magnet. Specifically, it can be constructed from a single tetradecagonal, annular piece of scintillator connected to arrays of silicon photomultipliers (SiPM). Use of monolithic scintillator can minimize interference with the EPRI scanner by virtually eliminating support structures, and maximizes detection sensitivity by removing scintillator gaps, both present in standard PET scanners. To capitalize upon the unique capabilities of the annular detector, a novel, flexible data acquisition (DAQ) system can be employed. In an embodiment, the temperature of the SiPMs can be stabilized/reduced by application of a unique immersion cooling technique developed for the unconventional geometry of the scanner. Immersion cooling also eliminates the metallic elements (Peltier coolers or cooling tubes) normally used to cool solid-state detectors. The EPRI component will implement the new rapid scan-EPR imaging method. This innovation enables rapid imaging with multi-line spin probes, as well as substantially improved sensitivity and SNR. A novel nested-element approach will be used to combine the two imaging components, as described herein. The animal enclosure necessary to anesthetize the animal will fit inside the EPR resonator, that will fit inside an RF shield, that will fit inside the EPRI rapid scan coils, that will fit inside the PET scanner, that fits inside a set of EPRI gradient coils. This design results in a very compact PET/EPRI insert, facilitating its mounting on a computer-controlled gantry that will move the insert into the dipole magnet required for EPRI. Finally, to minimize interactions between the rapidly switching gradient magnetic fields typically used in EPRI, and the PET electronics (induced eddy currents in the electronics), smoothly varying, sinusoidal gradient field switching will be employed.

An important advantage of utilizing a solid annulus of scintillator is the lack of gaps between detector modules and between detector elements present in most PET scanners, enhancing detection sensitivity.

Furthermore, studies with a prototype PET/EPRI scanner demonstrated the lack of cross-modality interference (including photon attenuation artifacts), as well as the ability to produce simultaneous images from the two systems that can be correlated with images acquired with a small animal MRI scanner.

In embodiments, an annular PET scanner can have advantages compared to those based on a ring of discrete, pixelated scintillator detector elements. For example, the amount of conductive material used to construct and mount discrete detector modules is eliminated, reducing possible distortion of the EPR magnetic field. The detector also can be made very compact (facilitating its integration into the limited volume in the EPRI scanner), since there are no support structures. Additionally, the scintillator gaps between adjacent detector modules that are created when they are formed into rings are not present, enhancing detection sensitivity. Furthermore, use of a single, continuous piece of scintillator enables correlation of DOI in the scintillator with the shape of the light distribution impinging upon the SiPMs.

Example 5

Adaptation of advanced imaging methods for use with small animals has transformed translational research. No longer are large numbers of animals necessary to perform biomedical experiments. Most preclinical scanners combine an anatomical imaging modality (magnetic resonance imaging (MRI) or x-ray computed tomography (CT)) with a functional imaging method (positron emission tomography (PET) or optical imaging). In this investigation, we propose the combination of two complementary, functional imaging methods: PET and electron paramagnetic resonance imaging (EPRI). Simultaneous PET-EPRI co-imaging has the potential to be a powerful tool for performing novel, in vivo investigations of biological systems, potentially leading to insights that can be translated into improved methods for diagnosis and treatments of disease.

Scientific Premise

PET utilizes administration of pico-molar concentrations of positron-emitting radiotracers in combination with rings of radiation detectors to measure intracellular physiological parameters such as glycolysis rates, DNA synthesis and cell replication. EPR enables interrogation of electron spins in free radicals that, when used in combination with paramagnetic probes, is an accurate method for measuring mostly extracellular physiologic processes. Among the most promising of these probes are phosphonated triarylmethyl radicals (pTAM) that possess very good stability, long relaxation times and narrow line widths (enhancing sensitivity and spatial resolution), making them particularly attractive for simultaneous in vivo measurements of pH, phosphate concentration (Pi) and $pO_2$. These parameters are especially important because they are critical aspects of tissue microenvironments in cancer and heart disease, but can be challenging to measure with MRI.

As with NMR, EPR is not inherently an imaging technique. Thus, its use was limited to making bulk measurements from relatively large areas of in vivo or ex vivo tissue. For many applications, however, it is desirable to map the spatial distribution of chemical environments. The first method for producing maps of pH, Pi and $pO_2$ utilized continuous wave RF emissions (CW-EPR), which, unfortunately, possesses non-optimal signal sensitivity due to excitation of small fractions of spins, and only parts of the spectrum per imaging cycle. Therefore, CW-EPR requires long acquisition times to produce images, up to two hours for 4D-imaging (3D-spatial; 1D-spectral). An alternative method is pulsed-EPR. In this process, the whole spectrum is excited simultaneously, resulting in shorter imaging times. This technique, however, requires EPR probes with long relaxation times and is not applicable to probes with broad multiline spectra, such as pTAMs.

Rapid scan-EPR imaging (RS-EPRI) occupies an intermediate niche between CW-EPR and pulsed-EPR. It measures transient signals, as in pulsed-EPRI, but uses CW excitation methods. Thus, the whole spin population is excited twice during the scan sequence, resulting in amplified signal intensity. Another factor that contributes to RS-EPRI signal enhancement is the rapid passage effect. In CW-EPRI a small percentage of the spin contributes to the signal. In RS-EPRI, however, the whole spin population contributes, resulting in up to a factor of 100 increase in sensitivity. The spin system experiences a short RF pulse as the magnetic field rapidly passes through resonance. When the magnetic field is scanned through resonance in a time that is short relative to the probe relaxation times, transient free induction decay (FID) oscillations are observed in the signal response. Unlike pulsed-EPRI, deadtime-free FID oscillations accelerate with time since they are driven by the changing magnetic fields. In RS-EPRI, the magnetic field is scanned through the EPR resonance tens-of-thousands of times per second, and the signals averaged. Deconvolution of the rapid scan signals result in the conventional absorption and dispersion signals. RS-EPRI methods that can be employed have a shortened total acquisition time (~2-5 min) for 4D-imaging of a mouse, and produce a one to two order of magnitude signal-to-noise (SNR) increase compared to conventional continuous wave-MRI, especially with multi-function probes (simultaneous $pO_2$ and pH measurements). Thus, micro-molar amounts of probe can be used, reducing physiologic effects and enhancing spectral resolution. Overhauser-MRI is also an option, but the amount RF power required may create an inhospitable environment for PET electronics.

A combined PET/EPRI scanner can address an unmet need for the ability to perform temporally correlated measurements of the intra- and extracellular components of physiological microenvironments. Specifically, quantification of intracellular parameters with PET complements the ability of EPRI to quantify extracellular parameters. Insights gained from measurements made with this system could potentially result in development of new methods for disease prevention, diagnosis and treatment. While the PET/EPRI scanner described in this proposal is designed for use in mice, the knowledge obtained from its construction may aid in identification and optimization of technologies necessary to design scanners intended for use with a wide range of animal models of disease (beyond mouse models) currently available to researchers, and eventually, perhaps, systems for human use.

It should be noted that PET-EPR imaging could be performed by sequentially scanning animals on separate systems (like the methodology used to combine fMRI and EPRI). This process, however, requires transport of the animals between two scanners, resulting in a time delay between measurements. The biochemical milieu of anesthetized mice, however, is not static; physiological parameters, such as glucose metabolism, pH, Pi and $pO_2$ levels may vary over short time periods (minutes to tens of minutes). Therefore, to ensure accurate, synchronized and unbiased measurements of interactions among components of physiology, it is important to perform simultaneous imaging to capture and correlated their temporal evolution. For example, if glucose metabolism rate, $pO_2$ and/or pH of the tissues change during the scanning time, this evolution will be captured on a similar time scale by both systems only if scanning is performed simultaneously (as demonstrated by simultaneous PET-MRI studies). Simultaneous scanning also facilitates accurate measurement of complex physiological responses to controlled administration of a chemical stimulus (breathing of carbogen, for example) that momentarily perturbs the animal's biochemistry. The combination of both systems into a single unit, also simplifies the registration process, since both scanners share a coordinate system. Finally, simultaneous scanning greatly increases the efficiency of the imaging process, which is important if many animals must be scanned in a short amount of time.

An example of an embodiment of a method of use of a PET/EPRI scanner is investigation of the hypothesis that progression to carcinogenesis is a somatic evolutionary process, similar in some ways to Darwinian evolution. The pre-malignant extracellular environment is often hypoxic, favoring neoplastic cells that exhibit increased glycolysis and hence glucose transport (overexpression of the GLUT-1 transporter) (the Warburg effect). This process results in reduced pH of the tumor microenvironment (TME) since glycolysis produces acidic byproducts. The acidic environment exerts selection pressure on cells to develop resistance to apoptosis and upregulation of membrane H+ transporters to maintain intracellular pH. As the tumor grows, angiogenesis progresses and $pO_2$ changes. The cells, however, continue to utilize glycolysis to produce energy. Ultimately, the increasingly acidic environment facilitates invasion of the neoplastic cells into adjacent tissues. A PET/EPRI scanner can provide a unique opportunity to observe this progression. Specifically, simultaneous, in vivo measurements of intracellular glycolysis rates (with FDG-PET) and extracellular $pO_2$ and pH (with pTAM-EPRI) in a cohort of animals exhibiting spontaneous tumors could be made at numerous time points to explore the dynamic relationship between glycolysis and TME.

While a combined PET/EPRI scanner could permit novel and potentially important experiments to be performed, construction of the system can be challenging. Integration of the two modalities requires special considerations to minimize mutual interactions between the systems that can produce sub-standard performance. Cross-modality interference can be assessed using measurements performed with phantoms, before and after integration.

B. Innovation

Integration of PET and EPRI has not previously been attempted. Development of the proposed system is a unique challenge, requiring innovative techniques as described herein to accomplish. The PET component can utilize a unique compact, design to reduce interference with the EPRI scanner, enhance performance and fit inside the confined space of the EPRI magnet. Specifically, it can be constructed from a single tetradecagonal, annular piece of scintillator connected to arrays of silicon photomultipliers (SiPM). Use of monolithic scintillator minimizes interference with the EPRI scanner by virtually eliminating support structures, and maximizes detection sensitivity by removing scintillator gaps, both present in standard PET scanners. To capitalize upon the unique capabilities of the annular detector, a novel, flexible DAQ system can be employed. The temperature of the SiPMs will be stabilized/reduced by application of a unique immersion cooling technique developed for the unconventional geometry of the scanner. Immersion cooling also eliminates the metallic elements (Peltier coolers or cooling tubes) normally used to cool solid-state detectors. The EPRI component will implement the new rapid scan-EPR imaging method. This innovation enables rapid imaging with multi-line spin probes, as well as substantially improved sensitivity and SNR. A novel nested-element approach can be used to combine the two imaging components. The animal enclosure necessary to anesthetize the animal will fit inside the EPR resonator, that will fit inside an RF shield, that will fit inside the EPRI rapid scan coils, that will fit inside the PET scanner, that fits inside a set of EPRI gradient coils. This design results in a very compact PET/EPRI insert, facilitating its mounting on a computer-controlled gantry that will move the insert into the dipole magnet required for EPRI. Finally, to minimize interactions between the rapidly switching gradient magnetic fields typically used in EPRI, and the PET electronics (induced eddy currents in the electronics), smoothly varying, sinusoidal gradient field switching will be employed.

2.1 Prototype PET Scanner Component Testing

As noted above, the PET component of the PET/EPRI scanner can utilize a novel design based on a monolithic annulus of scintillator to minimize the potential for magnetic field distortions, and eliminate loss of detection sensitivity caused by the presence of gaps between detector elements. Initial assessment of this geometry was performed using Monte Carlo simulations with the GATE software package. GATE is an advanced open source software package developed by the international OpenGATE collaboration to emulate the performance of PET and SPECT scanners, including effects of photon attenuation and Compton scattering. It has been extensively validated and used in numerous projects to evaluate new PET scanner designs. The modeled scanner comprised a 7.2 cm long annulus of scintillator (LYSO) with an outer diameter of 7.5 cm and inner diameter of 5 cm (FOV=4 cm). Fourteen 1.8×7.2 $cm^2$ facets were placed equidistantly around the outer surface of the annulus to permit attachment of SiPM arrays. The characteristics of the simulated SiPMs were representative of those that can be used in the actual system (4×4 arrays of 4×4 $mm^2$ (pitch=4.75 mm)). The two end surfaces of the annulus were blackened to prevent reflection of photons. Its inner surface was coated with D'Lambertian reflectors to diffusely reflect scintillation light, which enhances the ability to estimate the depth-of-interaction (DOI) of annihilation events in the scintillator.

Figure 15:
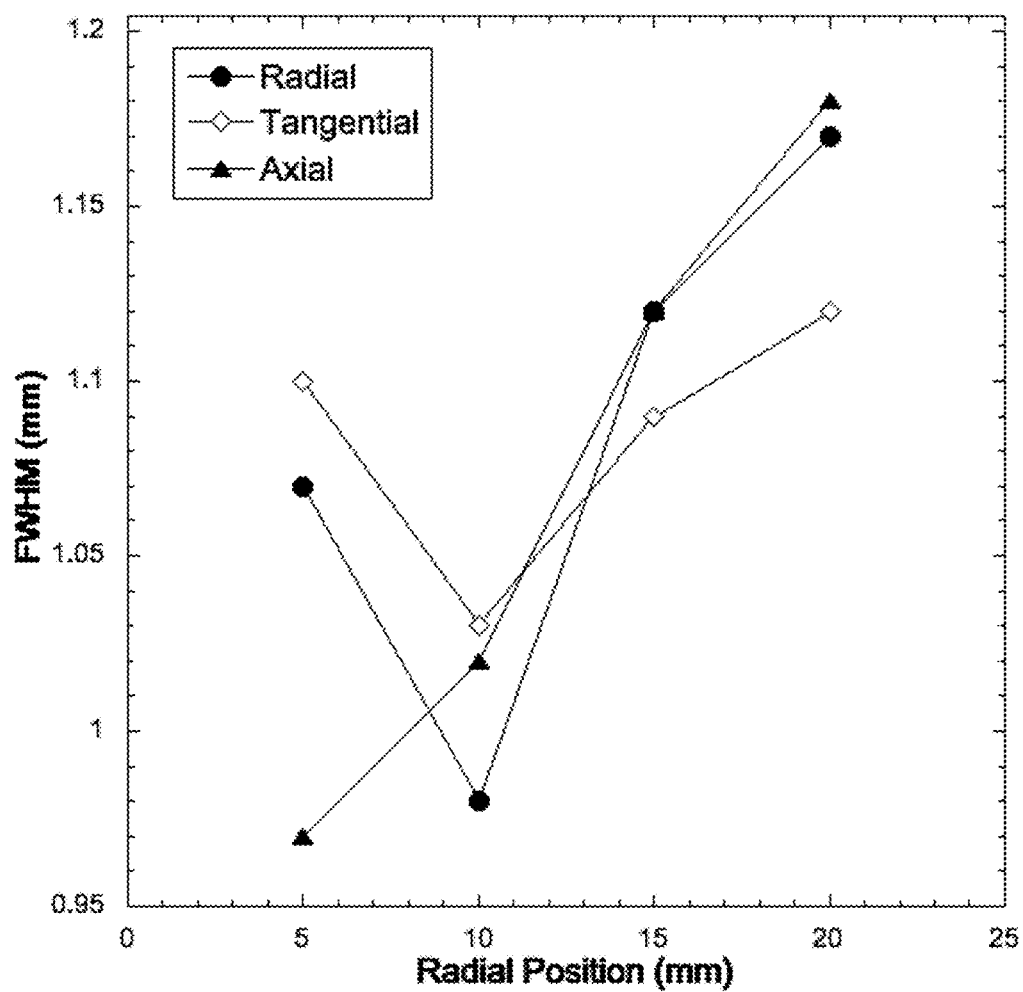
FIG. 15 is a plot of spatial resolution as a function of position.

In certain aspects, acquisition of data from the PET scanner first entailed simulation of annihilation photon interactions with the scintillator using GATE, and then transport of the scintillation photons resulting from these interactions to each SiPM in the arrays (emulating individual readout of the SiPM arrays). Simulated scanning with GATE produced a list mode data file; each line contained the three-dimensional coordinates and energy deposited in the scintillator for each of the coincident annihilation photons. These coordinates specified the actual locations of the events in the scintillator (xo, yo and zo), but not the ones that would be recorded by an actual PET scanner. This determination required introduction of the errors inherent in position calculations based on the distribution of scintillation light impinging on the SiPM arrays. To achieve this goal, photon transport was modeled using DETECT2000. This software is a Monte Carlo-based tool for simulating the behavior of optical systems, and has been utilized to evaluate the optical characteristics of PET detectors. Using this information, the original GATE-produced list mode file containing the actual positions of the events was transformed into one that incorporates the effects of positioning and DOI errors (x, y and z coordinates) due to photon transport. A set of sinograms spanning the entire scanner's field-of-view (FOV) was then created from the transformed list mode data. Images were reconstructed with either the single slice rebinned-filtered back-projection algorithm (SSRB-FBP) algorithm for NEMA-based measurement of spatial resolution or with OSEM reconstruction software for imaging of phantoms. The FWHMs of intensity profiles acquired from images of a point source were reported as spatial resolution. As the plot in FIG. 15 shows, the spatial resolution in all three dimensions is ~1.1 mm FWHM (SSRB-FBP), which compares favorably to small animal PET scanners based on arrays of discrete detector elements (1.63 mm to 2.32 mm FWHM). The results also compare well with other small animal PET scanners based on monolithic scintillator whose reported spatial resolutions range from 0.7 mm to 1.65 mm FWHM. Good resolution results are due in part to the confined nature of the photon distribution; 83% (range 62% to 96%) of the optical photons detected by the SiPM arrays were localized to three contiguous facets. These findings indicate that there is minimal negative effect from internal photon scattering in the annular scintillator. The relatively uniform resolution across the radius of the scanner is due to the application of DOI corrections. To date the highest resolution pre-clinical scanner was developed by the UC-Davis group, the reported spatial resolution is ~0.6 mm. This system utilizes traditional methods, employing pixelated arrays of very small detector elements coupled to PSAPDs. Its axial and transaxial FOVs are 7 mm and 2 mm, respectively, compared with 7.2 cm and 4 cm for our proposed system.

Figure 16:
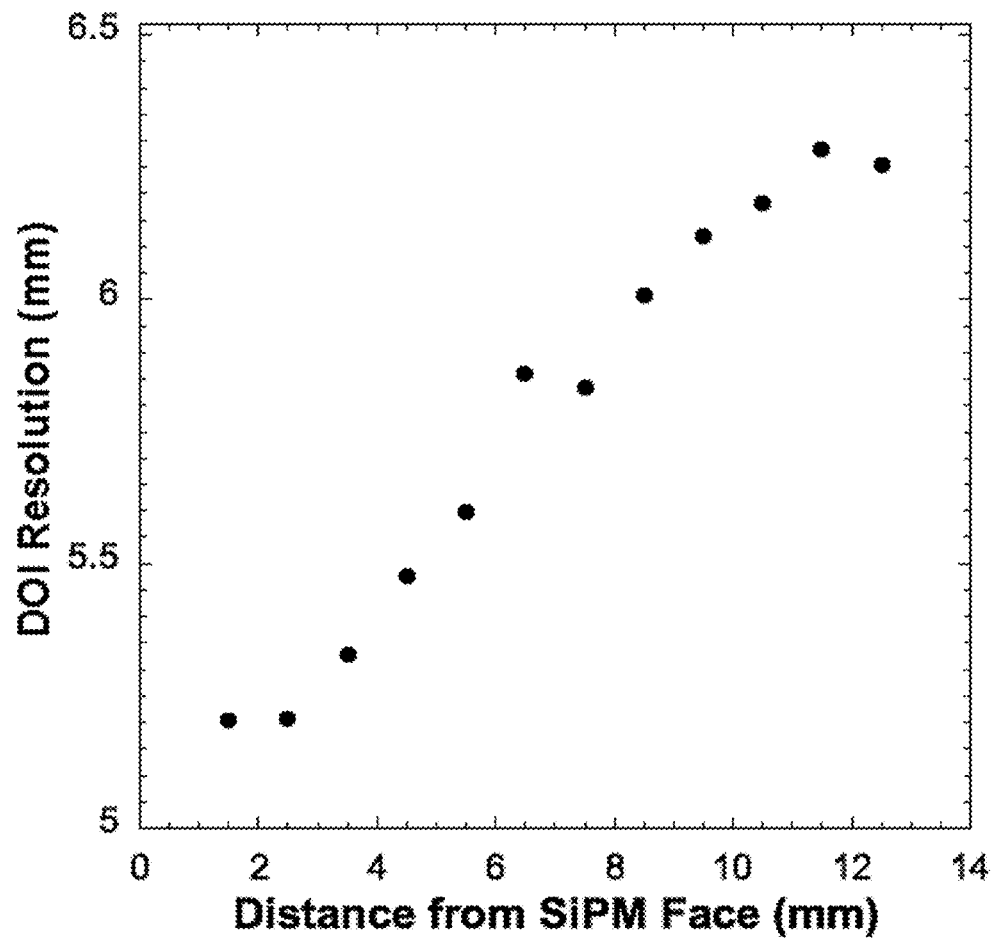
FIG. 16 is a plot of DOI resolution as a function of distance from SiPM face.

The plot in FIG. 16 shows that the accuracy of DOI measurements are related to the depth of the events. Specifically, DOI estimations for shallow events are slightly less accurate (mean DOI measurement resolution=6.3 mm FWHM) than for deep events, close to the surface of the SiPMs (mean DOI measurement resolution=5.2 mm FWHM). This difference is likely due to uncertainties caused by the reduced number of photons reaching the SiPMs for shallow events compared to deeper events, due to photon attenuation in the scintillator. The mean DOI resolution is slightly lower than that reported by van Dam, et al. for a detector based on monolithic scintillator. Note, that this level of DOI resolution was sufficient to effectively correct images for radial degradation in resolution, as demonstrated by the relatively uniform spatial resolution results (FIG. 15).

An important advantage of utilizing a solid annulus of scintillator is the lack of gaps between detector modules and between detector elements present in most PET scanners, enhancing detection sensitivity. Detection sensitivity was measured by simulating a 22Na point source at nine positions along the central axis of the scanner. These data were used to calculate detection sensitivity at each location. Peak sensitivity at the center of the scanner was 10.1% (energy window=350 to 650 keV), which compares well with the sensitivity measured for scanners utilizing arrays of discrete detector elements, (1.19% to 6.72%), those employing monolithic scintillator-based detectors (0.3% to 9%), and to the UC-Davis mouse scanner (0.68% (lower energy lower threshold=250 keV)).

FIG. 16: Plot of DOI Resolution as a Function of Distance from SiPM Face

Figures 17A, 17B:
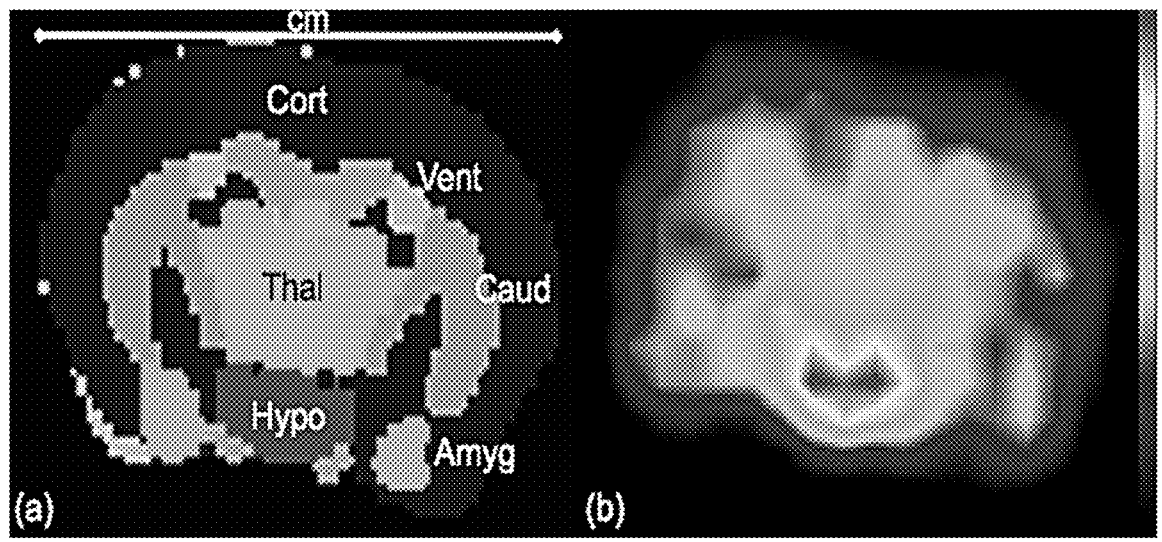
FIGS. 17A-17B are an images of the MOBY phantom.

To demonstrate the potential value of an annular PET scanner applied to imaging of a small animal, the brain section of the 4D Mouse Whole Body (MOBY) digital phantom (v2.0) was 'scanned' with the simulated annular PET scanner. The amount of activity in each of the phantom's structures was adjusted to simulate a 100 µCi injection of FDG. The elements of the embodiment of the EPRI scanner (described below) were included in the simulation. Thus, the effects of photon attenuation and Compton scatter in these structures were included in the data. An OSEM-reconstructed image of the phantom (corrected for positron range effects) from a 1 min scan is shown in FIGS. 17A-17B. Small structures such as the thalamus, hypothalamus, amygdala, caudoputamen and cortex are identifiable. Smaller structures, such as the ventricles, are not as clearly discernable. The results from these simulations aided in refinement of the design of the PET scanner's geometry and DAQ triggering electronics (described below).

FIGS. 17A-17B: Image of the MOBY phantom. FIG. 17A shows a MOBY phantom with major brain sections labeled (cortex (Cort), thalamus (Thal), hypothalamus (Hypo), caudoputamen (Caud), ventricles (Vent) and amygdala (Amyg)) labeled, and FIG. 17B is a PET image of the phantom.

2.2 Prototype Combined PET-EPRI Scanner

The potential advantages and cross-modality interactions between PET and EPRI scanners were explored by construction of a prototype combined system. The PET scanner used in this study was constructed at West Virginia University as part of a continuing effort to produce images of the brains of ambulatory subjects. It comprises a ring of twelve detector modules (inner diameter=21 cm). Each module contains a 32×32 array of polished LYSO detector elements (1.5 mm×1.5 mm×10 mm), separated by 0.07 mm thick ESR reflector (Proteus, Chagrin Falls, Ohio). The twelve scintillation blocks are individually coupled to 10×10 arrays of 3 mm×3 mm (4.85 mm pitch) S10362-series MPPCs (multi-pixel photon counters) (Hamamatsu Photonics, Shizuoka, Japan). The MPPCs are readout with multiplexed, 4ch-readout electronics (AiT Instruments, Newport News Va.). The forty-eight amplified analog signals are digitized with an FPGA-based, 64-channel data acquisition module (AiT Instruments, Newport News, Va.). These data are used to create three-dimensional maps of radiotracer distribution with the MLEM (Maximum-Likelihood Expectation-Maximization) iterative reconstruction algorithm. The spatial resolution of the system is 2.2 mm (SSRB-FBP) 5 mm from center of scanner (half of the proposed system's resolution) and peak detection sensitivity of 0.5% (a factor of twenty lower than the proposed system).

The EPR imager was constructed at West Virginia University as part of an ongoing effort to explore and advance EPRI methodology. It utilizes the recently developed rapid scan (RS) EPR technique (RS-EPR).

The EPRI resonator unit comprises an RF surface loop (into which the sample is placed) connected to a distributed capacitor network containing two 50Ω coaxial cables and a coupling unit that matches the resonance structure to the 50Ω transmission line. The unit also comprises a λ/2 balun. The constant magnetic field necessary to produce the EPR signals is supplied by a permanent dipole magnet (Ningbo Jansen NMR Technology, Co). It can have a pole-to-pole gap of 12.5 cm (a factor of four smaller than our proposed system) and produces a magnetic field of ~268 G corresponding to ~750 MHz for an EPR spin probe with a g-factor of ~2. Elements of a Helmholtz coil are mounted on the magnet poles to facilitate fine tuning of the magnetic field up to ~293 G (820 MHz). The EPR spectra of the trityl probe used in this investigation has two components, Gaussian and Lorentzian. The width of the Lorentzian component (EPRI-Lw) was extracted from the spectral data using a line fitting procedure; its value is related to the presence of oxygen, or other paramagnetic compounds. The integral of the EPR spectra intensity is related to probe concentration (EPRI-Conc). Four-dimensional images (three spatial axes and one spectral) of EPRI-Lw and EPRI-Conc were reconstructed using the iterative backprojection method. The nominal EPRI image voxel size is 0.25 mm×0.25 mm×0.25 mm.

A multi-modality phantom was designed and fabricated with a FormLabs (Somerville, Mass. USA) Form2 3D printer. It has an outer diameter of 10.7 mm and contains four 254 µl cylinders (3 mm inner diameter; length=36 mmm; center-to-center distance=4.6 mm). The cylinders were filled with specially-formulated, PET-EPR imaging solution. Specifically, an oxygen reporting spin probe, per-deuterated 'Finland' triarylmethyl (trityl) radical (dFT), was used to produce EPR signals. Since it is difficult to accurately control oxygen concentration in the phantom, 1 mM of gadolinium contrast agent (Gd-DTPA, BioPAL, Worcester, Mass. USA) was added to 1 mM of dFT to emulate the presence of oxygen. Gadolinium shortens the relaxation times of the EPR probe by the same exchange interaction mechanism as oxygen. The PET radiotracer 18F-FDG was added to the EPR probe solution to create the dual-modality tracer. Two variants of PET-EPRI imaging solution were created. One contained 1 mM of dFT, 1 mM of Gd and 25 µCi of FDG (defined as the Gd+F− solution). The second contained 1 mM of dFT and 49 µCi of FDG (defined as the GdoF+ solution). This concentration of dFT is comparable to that measured in vivo. Indigenous oxygen in the solutions was removed by adding glucose (10 mM, Sigma Aldrich, Cleveland, Ohio USA) and glucose oxidase (500 U/ml, Sigma Aldrich, Cleveland, Ohio USA). To make up the required volume of the samples (254 µl), appropriate amounts of 0.1 M Na-phosphate buffer (pH=7.4) were added. The phantom was filled such that diagonally opposed cylinders contained the same solution type.

To create the prototype PET/EPRI scanner, the PET detector ring was placed in the center of the dipole magnet (to permit access to the center of the PET scanner, it was tilted by approximately 20°) (FIG. 11). The EPR system's rapid scan coils were placed in the center of the PET ring. The EPR RF loop holding the phantom was inserted into the center of the PET-RS-coil combination. The orientation of the RF field is parallel to the axis of the loop. PET and EPRI data were obtained simultaneously for 3 min. Images were created as described above. Following the PET-EPRI scan, the phantom was placed in a 1 T small animal our ICON™ MRI scanner (Bruker, Billerica, Mass. USA) (T1 FLASH; TR=41 ms; TE=4.8 ms; flip angle=30°; image voxel size=0.25 mm×0.25 mm×2.4 mm). Prior to registration, the MR, PET and EPR images underwent rigid body rotation and scaling based on their relative orientations and image pixel sizes. Registration was performed by overlaying the transformed images utilizing the Photoshop™ image processing software (San Jose, Calif. USA). While PET and EPRI can produce quantitative images, for this initial investigation it was chosen to only make qualitative comparisons between images from the modalities to simplify imaging processing. Thus, image intensities are utilized to represent relative radiotracer concentration, dFT probe concentration and simulated oxygen concentration.

FIG. 11: Picture of the complete PET-EPRI system (orientation of the magnetic field is shown).

FIG. 12A shows the T1-weighted MRI image of the phantom (the light gray semi-circles at the top corners are images of two small vials of water included with the phantom to facilitate tuning of the MRI scanner). The PET image in FIG. 12B illustrates the differences in FDG concentration of the two solutions based on relative image intensity. Importantly, there are no photon attenuation artifacts apparent in the images. FIG. 12C shows a map of the Lorentzian contribution to the EPR signal line width (EPRI-Lw), which is related to $pO_2$ in the sample (line width is measured in milli-Gauss). The image in FIG. 12D is a map of the intensity integral of the EPR spectra related to the concentration of dFT in the solutions (EPRI-Conc). Importantly, there are no cross-modality-related artifacts in either the PET or EPR images.

Very high spatial resolution and detection sensitivity for the PET component of the proposed system can be acquired. Furthermore, studies with a prototype PET/EPRI scanner demonstrated the lack of cross-modality interference (including photon attenuation artifacts), as well as the ability to produce simultaneous images from the two systems that can be correlated with images acquired with our small animal MRI scanner. Use of this scanner may be restricted due to the restricted size of the imaging area (FIG. 11).

FIGS. 12A-12D: PET-EPR images of the multi-modality phantom: a) MRI image showing the presence and absence of Gd ($Gd^+$ or $Gd^0$), and the presence of high or low concentration of $^{18}F$ ($F^+$ or $F^-$), b) PET image (image intensity is related to FDG concentration), c) EPR image of Lorentzian line width (EPRI-Lw) (image intensity is related to oxygen concentration simulated using Gd) and d) EPR image of dFT concentration (image intensity is related to dFT concentration).

Figure 18:
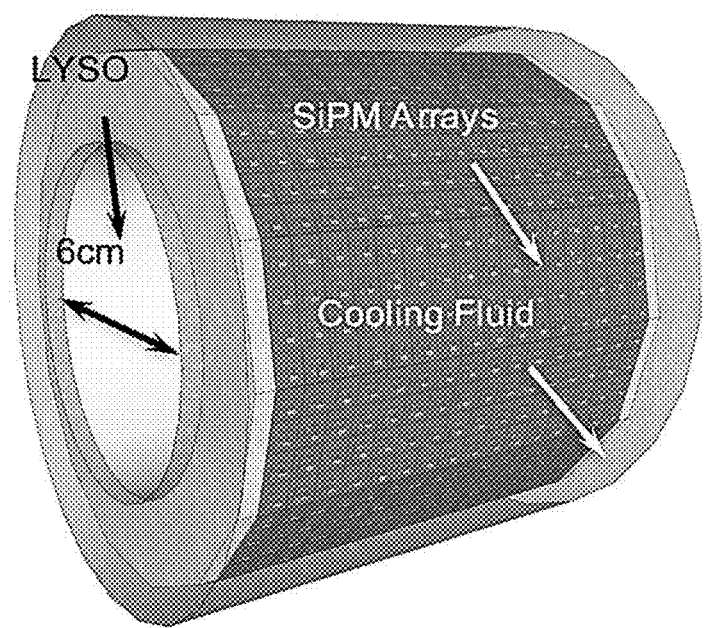
FIG. 18 is a schematic drawing of an annular PET scanner.

Construction of the PET Component:

Detector Design: As noted above, the PET component of the system can comprise a monolithic annulus of LYSO, attached to arrays of SiPMs. The annulus will be 7.2 cm long with an outer diameter of 8.2 cm and inner diameter of 6 cm. The scanner's imaging FOV will have a nominal diameter of 5 cm and axial length of 7 cm. (appropriate for imaging of mice). Fourteen 1.8 cm-wide facets can be machined equidistantly around the outer surface of the annulus (FIG. 18). In addition to the performance benefits produced by this design, use of a continuous annulus reduces price of the scintillator compared to a similar-sized ring of discrete detectors comprising arrays of small elements (see price quote and mechanical drawing). Arrays of SiPMs, like the ones simulated in studies as described herein, will be assembled and attached to the facets. SiPMs are compact and possess gains on the order of PMTs, but they are not affected by magnetic fields. Their performance is, however, influenced by temperature; signal gain is increased and dark current reduced by lowering their temperature. The standard methods for cooling SiPMs utilize Peltier devices or circulation of cooled liquid through tubes indirectly coupled to the devices. The ancillary hardware necessary to implement these methods is bulky and can distort magnetic fields. Hence, in embodiments according to the present disclosure, the temperature of the SiPMs can be regulated by immersing them in cooled, non-electrically conductive, non-paramagnetic, fluid circulated through the sealed enclosure surrounding the detector. The fluid will be cooled to 10° C. by a mini-chiller.

As previously noted and demonstrated by the PENN-PET and AnnPET scanners, an annular PET scanner has advantages compared to those based on a ring of discrete, pixelated scintillator detector elements. For example, the amount of conductive material used to construct and mount discrete detector modules is eliminated, reducing possible distortion of the EPR magnetic field. The detector also can be made very compact (facilitating its integration into the limited volume in the EPRI scanner), since there are no support structures. Additionally, the scintillator gaps between adjacent detector modules that are created when they are formed into rings are not present, enhancing detection sensitivity. Furthermore, use of a single, continuous piece of scintillator enables correlation of DOI in the scintillator with the shape of the light distribution impinging upon the SiPMs. DOI estimates will be used to correct for the parallax effect, which is especially important for a PET scanner with a small bore. Finally, previous studies utilizing detector modules based on monolithic scintillator report degraded performance in regions where modules abut, due to distortions of the light distribution in these areas. The annular scanner does not utilize rings of discrete modules, so this effect is not present.

FIG. 18: Schematic Drawing of the Annular PET Scanner.

Data Acquisition Electronics: To achieve high spatial resolution in all three dimensions, each of the fourteen facets can be covered with four detector sub-units, each comprising 4×4 arrays of 4×4 mm$^2$ (pitch=4.5 mm) SiPMs. The signals from individual SiPMs in the array will be readout, unlike the multiplexing schemes used in many scanners. Individual readout maximizes the ability to detect slight differences in the scintillation light distributions used to identify event positioning, making it possible to achieve the very good spatial resolution (~1 mm) expected for a system as described herein even though 4×4 mm$^2$ SiPMs are used. Each sub-unit can therefore produce 4×4=16 individual outputs. Since each facet can contain four subunits, a total of sixty-four outputs (4 sub-units×16) can be produced per facet, resulting in 896 (64×14 facets) total analog SiPM outputs from the PET scanner. The readout electronics will also produce a single sum signal representing the total amount of light detected by a sub-unit, resulting in fifty-six total signals (4 sums×4 facets). The sum of the amplitudes of these signals are proportional to the amount of light detected by the SiPMs. The readout electronics are also connected to interface modules that provide bias voltage to the SiPMs and amplify the analog outputs. The SiPM position signals will be routed to a maximum of twenty-three, 40-channel integrating FPGA-based ADCs. The ADCs will be triggered via the specialized trigger electronics described below.

A novel, zone event triggering system can be constructed to efficiently process the data (FIG. 1). Specifically, the sum outputs from individual SiPM sub-units will be grouped into variable-sized zones. The electronics can identify the position of the maximum SiPM sum signal. Signals from adjacent sub-units can then be summed (the number of sub-units to be included will be selectable). Thus, the positions and size of the zones are not fixed, as in the fixed zone scheme used by the PENN-PET scanner. Based on preliminary studies (described above), signals from three sub-units adjoining the primary sub-unit can sample an average of 83% of the scintillation light detected for each event, so this trigger zone size can be employed and effectiveness assessed. The sum of the amplitude signals from the grouped sub-units is representative of the energy deposited in the scintillator. These signals will be amplitude-discriminated (lower threshold will be adjustable, nominally 350 keV; upper threshold=650 keV) and then divided into two data streams: one set of signals delayed and routed to an addressable switching unit, the other to a coincidence pre-processor. The coincidence pre-processor will be based on a Xilinx complex programmable logic device (CPLD). The pre-processor will form the trigger zones using the discriminated sub-unit outputs. It will implement a bi-signal programmed matrix coincidence logic scheme with a relatively wide timing window (25-30 ns). Apart from producing a TTL coincidence signal upon determination of a coincidence, it can also set a position register containing the addresses of the sub-units involved in the coincidence. This information can be used by an addressable switching unit to route the appropriate delayed sum signals to a coincidence unit for final determination of a coincidence using a selectable coincidence window (nominally 6 ns). The coincidence pre-processor unit makes it possible to determine the identities of the detectors involved in the coincidence and reduces the number of non-coincidence events that are processed by the full set of trigger electronics. Thus, the number of events processed by the coincidence unit will be limited, reducing dead time and maximizing count rate efficiency, which is important for acquiring the high temporal resolution PET data necessary to accurately calculate compartmental model parameters. If a coincidence is detected, the addressable logic unit will distribute the trigger pulses to the appropriate ADCs (determined by the CLPD-supplied addresses) for digitization of the individual analog SiPM signals. The digitized data will also be routed to a series of networked CPUs, where the event's x- and y-coordinate, as well as its DOI and energy, will be determined using calculations performed on the signals in tandem with previously measured calibration tables (described below).

FIG. 1: Schematic Drawing of the PET Trigger Electronics.

The x- and y-coordinates can be calculated from the digitized outputs by determining the 2D-center-of-mass of the scintillation light distribution recorded by the SiPMs. The z-coordinates (equivalent to DOI) will be estimated by taking the ratio of the total number of counts in the photon distribution (calculated by the DAQ trigger electronics) to its peak intensity (N/I). Note that non-uniformities of light output in the scintillator (specified by the manufacturer to be approximately ±1.5%), which could affect the calculation of DOI, will be normalized via the N/I ratio method used to estimate event depth.

Determination of the x-y positions of the events and their DOI require calculations of the correlations between signals acquired from the scanner and event position via calibration tables. To perform these calculations, a device will be created using sources of 511 keV photons comprising positron-emitter sources in a lead collimator mounted on a motor-controlled gantry. This device will position the sources at any cylindrical coordinate inside the bore of the detector. To calibrate the x- and y-coordinate calculation, the locations of the sources will be correlated with the signals from the DAQ electronics. Additionally, the effects of light production and collection variability in determination of event position (x- and y-coordinates) will be corrected by incorporating data acquired from a uniform flood phantom into the calibration process. These data will also be used to correlate event amplitude with energy. Calibration of the DOI estimation will be performed by employing a technique used with current continuous scintillator-based detectors. Specifically, the intensity distribution of the photons emitted by collimated sources in the scintillator will be calculated using GATE simulations (like the one described in the Preliminary Studies section). The distributions will be subdivided into ten, 1 mm-thick bins. Next, the data collected during the x-y calibration procedure (described above) will be used to estimate DOI for each event via the N/I ratio method. The resulting values will then be binned into 1 mm-thick segments. This distribution will be correlated with the simulated distribution, creating tables relating measured N/I to the known DOIs determined from the Monte-Carlo simulations; likely resulting in higher DOI resolution than achieved in our preliminary studies. These methods permit the system to achieve spatial resolution approaching 1 mm, even though the SiPMs are 4×4 mm$^2$.

PET Image Reconstruction: Data from the PET scanner will be reconstructed by applying the OSEM-based software developed to create the PET images shown in the Preliminary Studies section (FIGS. 17A-17B and 12A-12D). Since initially, the new scanner may not be able to produce an attenuation map, the data for the small amount photon attenuation in a mouse may not be corrected for. While the EPRI elements located inside the bore of the PET scanner can be constructed with low attenuation materials and did not noticeably impact the simulated and actual PET images (FIGS. 12A-12D), the small level of photon attenuation can be corrected using a photon attenuation map calculated from a segmented CT image of the structures. This map can be integrated into the reconstruction software. Compton scattering from the mouse will be small (due to the low mass of the animal) and unlikely to tangibly contaminate the data. Scattering from the EPRI components, however, may contribute a significant Compton scattering signal. To address this phenomenon, a single scatter model with a segmented CT image of the components can be used to estimate the scatter distribution, which can then be incorporated into the reconstruction algorithm. In the current design of the DAQ electronics, it is not possible to directly estimate random coincidence rates (using delayed coincidence electronics, for example). Instead, random coincidence rates will be estimated from single event rates. The unique truncated annular geometry possesses a potential complication that may affect reconstruction fidelity not present in standard PET scanners. Specifically, the thickness of the scintillator is not radially uniform due to the presence of the facets. The thinnest dimension can be 9.97 mm (distance from the center of facet to inner surface); the thickest dimension can be 11.0 mm (distance from the seam between two facets to inner surface). Thus, the detection efficiency of the individual rays may not be uniform, potentially resulting in image artifacts. Our calculations, however, indicate that the absorption difference between these two extremes in path length is ~9%, which is unlikely to produce deleterious effects on the images. Finally, due to the high resolution of the system, the effect of positron range (even for positrons emitted by 18F) may affect resolution. Thus, images can be corrected using a modified, 3D version of Derenzo's 3D-deconvolution method based on the positron range distribution for 18F.

Initial Testing: Prior to integration with the EPRI scanner, performance of the PET scanner can be assessed using the NEMA NU4-2008 protocols. Spatial resolution, detection sensitivity, noise equivalent count rate (NECR) and contrast recovery will be measured. In addition to spatial resolution, assessment of count rate performance (NECR) is especially important, given the high event rates expected to be produced by the enhanced detection sensitivity of our geometry and presence of radioactive Lutetium in LYSO. While the DAQ hardware is intended to efficiently process events, it is important to assess whether the design is successful in reducing dead time and maximizing count rate performance.

Construction of the EPRI Component:

Construction of the EPRI Module: The EPRI module can comprise a bi-modal transmit-receive resonator (frequency=~1100 MHz), RF shielding, RS-coils and gradients package as a nested cylinder (FIGS. 2A-2B). This design can provide improved sensitivity and detection uniformity compared to the loop antenna used in the preliminary studies. Thus, improved 4D-EPR image quality/uniformity is expected compared to the images in FIGS. 12A-12D. The RS-scan coils can be wound on the surface of a low-density plastic cylinder with a diameter large enough to fit outside the resonator and shield. They can produce 20-30 G peak-to-peak fields at ~40 kHz. To reduce RF and microphonic coupling between the resonator and RS-coils, an RF shield can be placed between the two devices. The shield can comprise a low-density plastic cylinder coated with copper foil strips that will be virtually transparent to annihilation photons and field scans, and pieces of foam to dampen vibration.

Three gradient coils (x-, y- and z-gradients) can provide correlation between RF emissions and spatial reference frames required for creating EPR images. A set of Helmholtz coils can be used to create the z-gradients, while the x- and y-gradients can be manufactured using the compact 'fingerprint' configuration common in MR spectrometers. The complex wiring patterns used in these devices can first be modeled in Matlab. Based on the results from the modeling, jigs for the optimal shape of the gradient coils can be 3D-printed. Wire will be wound into the appropriate configurations using these jigs to create the coils. In standard EPRI scanners, the gradient fields are rapidly switched in sequence relative to each other. This method, however, could induce eddy currents in the PET scanner electronics, potentially creating image artifacts. To reduce this interference, the standard saw-tooth switching pattern can be replaced by smoothly varying sinusoidal waveforms (frequencies of 16.5 Hz, 59 Hz and 37 Hz, for Gx, Gy, and Gz, respectively, for example), producing gradient strengths of >1 G/mm. This approach can have the advantage that slowly changing gradients should produce minimal or no interfere with the PET electronics. The maximum gradient amplitude will be √3 times greater than in the standard approach. This gradient scheme will not adversely affect imaging because the sampling period (10 µs) is a small fraction of the gradient waveform. It, however, can require streaming of large datasets and post-processing due to the rapid sampling used in this method, hence the necessity for advanced computing systems. Prior to integration with the PET scanner, the components of the EPR system that are to be placed inside the PET scanner can be tested by acquiring spectra from samples of an EPR probe (pTAM). This probe is sensitive to pH (spectral sensitivity=$3\Delta ap/\Delta pH \approx 0.5$ G/pH unit; accuracy of pH measurements=±0.05 pH units) and can also provide accurate $pO_2$ measurements (spectral sensitivity=$\Delta H/\Delta pO_2 \approx 0.4$ mG/mmHg; accuracy mmHg).

Construction of the Animal Pod: It is standard practice in small animal imaging to anesthetize the animals to minimize stress and motion during a scan. An enclosed animal pod designed to fit inside the EPRI module can be employed in systems as described herein. It can comprise a low-density plastic tube, with a positioning fixture, gas inlet, exhaust port, instrumentation ports, animal warming apparatus and catheter port located in one of the endcaps. The positioning fixture will be a platform on which the animal is placed while in the pod. The animal's temperature (body temperature) can be stabilized with a heating pad attached to the animal fixture and monitored using an EPR-compatible thermometer. Finally, a pattern of fiducial markers filled with distilled water mixed with 18F and MR contrast agent can be mounted in recessed areas on the surface of the pod. These markers are necessary to register the PET, EPR and MR images of the mouse. MRI may be necessary in some aspects to provide anatomical images of the mouse for correlation with the PET/ERP images. The animal pod can be designed to be unobtrusively positioned in the bore of the Brüker ICON™ small animal 1T MRI scanner for the acquisition of such images.

EPR Imaging: EPR images can be reconstructed using the spectral-spatial algorithm developed as described above. RS-EPR signals can be measured for N discrete values of the rotating gradients. The signals can be de-convolved to produce EPR spectra projections. The projections can be Fourier transformed and truncated to include M points of interest. The result can be an N×M dataset that can be divided into M subsets of size N, corresponding to each spatial frequency in the Fourier domain. A system of linear equations can then be solved for each subset using Tikhonov regularization to produce M 3D images for each frequency, from which a 4D image will be assembled. Application of inverse Fourier transforms in the spatial frequency dimension results in a 4D spectral-spatial image matrix. EPR spectra corresponding to each voxel in the images will be fit using the known line-shape functions to extract pH and $pO_2$. Thus, the 4D image matrix will be converted to a set of 3D maps for each of these parameters, like the methods used to create the images in FIGS. 12A-12D. EPRI spatial resolution is given by R=LW/Gr (where LW is the spectral line width (<0.2 G for our EPR probes) and Gr is the magnetic gradient strength (~1 G/mm)). Thus, EPRI resolution of systems as described herein can be between at least 0.2 mm. SNR can be determined by LW, Gr and affinity of the probe. Given these factors, and the enhanced SNR capabilities of the rapid scan approach, a SNR of >20 is estimated, sufficient to achieve sub-millimeter spatial resolution.

FIG. 1: Schematic Drawing of the PET/EPRI Insert.

System Integration:

PET/EPRI Scanner Integration: The final stage in creation of the PET/ERPI insert. This unit includes the ERPI module, the PET scanner and animal pod. The integration process can be simplified by our nested component design (FIG. 1). The complete PET/EPRI unit can be placed in the 415 G magnet of our clinical EPRI system. The advantage of this system, compared to others is its large pole-to-pole separation (50 cm), which provides ample space for the insert. Since the EPR magnet is a dipole, and the axis of the PET/EPRI insert bore must be parallel to the magnetic field direction, access to the center of the PET scanner will be obscured by the magnet's poles. To address this limitation, the PET/EPRI insert can be mounted on a non-electrically-conducting track connected to the scanner gantry (FIGS. 2A-2B). The track can permit the insert to be moved out of the magnet to facilitate placement of the animal in the insert and into the magnet for scanning. This motion will be performed using a computer-controlled DC-stepping motor linked to the track. The electrical, data acquisition and control cables, in addition to tubes carrying cooling liquid, can pass into the gantry via a set of conduits, continue through a circular cable carrier, and into a second set of conduits for final connection to the insert.

PET-EPR Image Registration: PET-EPR image registration will be accomplished by application of translation-rotation transformation matrices. Determination of these matrices can be based on calculations performed using the images of arrays of PET-EPRI fiducial markers placed on a fixture connected to the animal enclosure. Calculation of the transformation matrices will be performed in two steps on images of the markers. In the first stage, rigid motion and global affine (translation, scaling and rotation), transformation-based registration will be performed. The similarity measure between images of the markers from both modalities will be based on mutual intensity. An iterative, exhaustive search strategy can be employed for these tasks. While the exhaustive search helps reduce the local minima problem, it can considerably increase calculation time. For initial iterations, the search step will be relatively large. In subsequent iterations, the search step can be decreased. The large initial step will speed up the process; while later smaller steps will ensure that the accuracy of the final registration is not compromised. For markers with high levels of dissimilarity, a local non-rigid registration will be applied. Once the transformation matrices are calculated, the process does not have to be repeated for every set of images. Registration of PET/EPR images with images acquired with the ICON™ 1T small animal MRI scanner will be performed using the methodology described by Chow, et al. for calculation of transformation matrices using image sets acquired on different scanners. Display of the images from the individual scanners can be performed using software created with Interactive Data Language (IDL). Registered images can be displayed using the AMIDE software package.

FIGS. 2A-2B: Schematic Drawings of the PET/EPRI Scanner. a) Animal Loading and b) Scanning Configurations.

Integrated PET/EPRI Scanner Testing: While initial investigations of combined PET-EPRI imaging indicated no discernable cross-modality effects, the NEMA NU4-2008 testing protocols performed on the PET scanner and acquisition of EPR spectra performed prior to integration can be repeated and compared. Additionally, to assess the ability of the system to image small volumes of radiotracer and EPR probes, a modified, 3D-Rose-Burger contrast phantom can be constructed using 3D-printing techniques. The phantom will contain an array of small spheres embedded in a background signal region. The diameters of the spheres (five per row) can decrease in size from left to right (diameters=4, 3, 2, 1 and 0.5 mm). Contrast with background can vary with rows (there will be five rows). The $pO_2$ level can increase from the top to bottom row in evenly spaced increments; pH can decrease from top to bottom row in evenly spaced increments. Levels of $pO_2$ can be controlled by bubbling oxygen gas through a distilled water solution containing the pTAM EPR probe. The solution's pH can be adjusted to the desired value by adding small aliquots of HCl or NaOH. Additionally, 18F will be added to the solution used to vary $pO_2$ and pH to produce contrast ratios representative of FDG uptake in breast cancer (20:1 to 2:1). The phantom can then be imaged. Contrast-recovery-coefficients (CRC) will be measured for 18F, $pO_2$ and pH for all the spheres. These results can permit one to assess the system's sensitivity to small differences in tissue microenvironments.

In embodiments of the present disclosure, FDG-PET in combination with pTAM-EPRI can be used to spatially map and quantify tumor glucose metabolism, $pO_2$ and pH.

In embodiments of methods of use, imaging of small animals (mice, for example) can be undertaken. In an embodiment, animal preparations can begin with tail vein cannulation with a catheter. In an embodiment, isoflurane can then be administered in an infusion box, followed by insertion of the monitoring catheters. In an embodiment, mice can be injected with a dye, propidium iodide for example, for quantitative cell death measures. The sedated animal can be placed in the animal pod, which can then put into the PET/EPRI scanner. The pTAM probe can be injected through the tail catheter and the EPR imaging started. It is expected that the pTAM probe can provide sufficient EPRI signal at a dose between 0.2 and 0.4 mmol/kg body weight. Note that the pTAM probe is hydrophilic, and remains extracellular with minimal toxicity to the mouse, as confirmed by recent cytotoxicity studies. One of the advantages of trityl-based probes is their high stability in vivo (half-life of several hours to more than 24 h depending on the structure of the compound. Immediately following EPR probe infusion, up to ~100 µCi of FDG and ~1.5 µCi of 2-14C-DG can be injected as a bolus and PET scanning initiated. The use of 14C-DG can be required to permit post-scan histochemical analyses to occur before autoradiography (the uptake of FDG and CDG are equivalent in tissue). The half-life of 18F (110 min) limits the time available for tissue processing before the amount of activity is too low to produce accurate autoradiographs and perform the measures such as immunohistochemical analyses, whereas the long half-life of 14C (5,730 years) does not present this limitation.

Typically, PET/ERPI scanning will performed for ~5 min. Since the PET data is stored in time-stamped listmode format, it can be sorted into arbitrary time bins, maximizing the flexibility of data analysis methods. Initially, a sampling sequence can be used based loosely on a sequence used for dynamic FDG-PET mouse imaging (8×5 s, 4×30 s, 2×70 s). It is important to note that the high detection sensitivity and count rate performance of the PET component can permit the acquisition of high count density for relatively short scans, facilitating use of higher temporal sampling rates, and thus shorter total acquisition times compared to most other pre-clinical scanners. Tissue activity curves can be acquired from the reconstructed PET images produced for each time segment. The arterial input function can be obtained by drawing an ROI on the vena cava (partial volume correction will be applied using the anatomical MRI images of this structure). The resulting data can be used with three-compartment modeling techniques to calculate parametric images of glucose metabolism rates. It can also be possible to acquire short, non-dynamic PET scans (60 s or less) to produce semi-quantitative measures of tissue function, such as standardized uptake values (SUV). The ability to rapidly produce 4D-EPRI images (as demonstrated above) means that serial EPR measurements can be acquired during the dynamic PET protocol to track changes in TME during this time. The EPR images of $pO_2$ and pH can be registered with the parametric PET images using the methods described above. MR imaging of the mouse can be performed to define the outlines of anatomical regions of interest, for example tumors, (T1 and T2 weighted) by placing the animal pod in the bore of an MR scanner, such as an ICON™ 1T small animal MRI, prior to PET/EPRI scanning.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

Unless defined otherwise, all technical and scientific terms used have the same meaning as commonly understood by one of ordinary skill in the art to which this disclosure belongs. Although any methods and materials similar or equivalent to those described can also be used in the practice or testing of the present disclosure, the preferred methods and materials are now described.

All publications and patents cited in this specification are incorporated by reference as if each individual publication or patent were specifically and individually indicated to be incorporated by reference and are incorporated by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could differ from the actual publication dates that may need to be independently confirmed.

Therefore, the following is claimed:

1. A positron emission tomography (PET)-electron paramagnetic resonance imaging (EPRI) system, comprising:
   a PET-EPR insert comprising:
      an EPR resonator comprising:
         a resonator,
         a shield encircling the resonator, and
         one or more rapid scan coils (RS-coils) positioned around the shield opposite the resonator, the shield configured to prevent electrical coupling between the RS-coils and the resonator while being transparent to annihilation photons and magnetic field scans;
      a PET scanner comprising one or more solid-state photodetectors, the EPR resonator configured to nest inside an inner diameter of the PET scanner; and
      a subject module configured to house a subject for scanning, the subject module removably insertable within an inner diameter of the resonator.

2. The PET-EPRI system of claim 1, wherein the PET scanner has a ring geometry with the inner diameter.

3. The PET-EPRI system of claim 1, wherein the PET-EPR insert further comprises gradient coils surrounding an outer diameter of the PET scanner.

4. The PET-EPRI system of claim 1, further comprising one or more magnets configured to provide a magnetic field to the EPR resonator.

5. The PET-EPRI system of claim 4, wherein the one or more magnets are permanent magnets or electromagnets, individually or in combination.

6. The PET-EPRI system of claim 1, wherein the system is configured to circulate cooling fluid through or within the EPR resonator, the PET scanner, or both.

7. The PET-EPRI system of claim 1, further comprising a computer-controlled gantry configured to transport the PET-EPR insert into one or more magnets for scanning and house electronic leads to and from the EPR module and PET scanner.

8. The PET-EPRI system of claim 1, wherein the subject module is configured to modulate temperature inside the module or of the subject.

9. The PET-EPRI system of claim 1, wherein the subject module is configured to modulate anesthesia provided to the subject housed in the subject module.

10. The PET-EPRI system of claim 1, wherein the subject module is configured to monitor physiological parameters of the subject housed in the subject module.

11. The PET-EPRI system of claim 1, wherein the one or more solid-state photodetectors comprise one or more photomultipliers coupled to one or more radiation-sensitive scintillators.

12. The PET-EPRI system of claim 1, further comprising a computing device.

13. The PET-EPRI system of claim 1, wherein the shield comprises plastic coated with copper foil strips.

14. The PET-EPRI system of claim 13, wherein the shield comprises foam to dampen vibrations.

15. The PET-EPRI system of claim 1, wherein the subject module comprises fiducial markers mounted in recessed areas on a surface of the subject module.

16. The PET-EPRI system of claim 15, wherein the fiducial markers comprise a pattern of fiducial markers filled with distilled water mixed with a contrast agent.

17. The PET-EPRI system of claim 7, wherein the computer-controlled gantry is constructed from non-magnetic materials that produce no EPR signals.

* * * * *